United States Patent
Ullrich

(10) Patent No.: US 10,787,700 B2
(45) Date of Patent: *Sep. 29, 2020

(54) METHODS FOR DETECTING MULTIPLE NUCLEIC ACIDS IN A SAMPLE USING REPORTER COMPOUNDS AND BINDING MEMBERS THEREOF

(71) Applicant: ABBOTT RAPID DIAGNOSTICS JENA GMBH, Jena (DE)

(72) Inventor: Thomas Ullrich, Jena (DE)

(73) Assignee: ABBOTT RAPID DIAGNOSTICS JENA GMBH, Jena (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/371,268

(22) Filed: Apr. 1, 2019

(65) Prior Publication Data

US 2019/0376125 A1 Dec. 12, 2019

Related U.S. Application Data

(63) Continuation of application No. 15/116,185, filed as application No. PCT/EP2015/053759 on Feb. 23, 2015, now Pat. No. 10,246,737.

(30) Foreign Application Priority Data

Feb. 21, 2014 (GB) .................................. 1403076.1

(51) Int. Cl.
| | |
|---|---|
| *C12P 19/34* | (2006.01) |
| *C12Q 1/6818* | (2018.01) |
| *C12Q 1/6844* | (2018.01) |
| *B01L 3/00* | (2006.01) |
| *G01N 33/52* | (2006.01) |
| *G01N 33/542* | (2006.01) |
| *G01N 21/64* | (2006.01) |

(52) U.S. Cl.
CPC ...... *C12Q 1/6818* (2013.01); *B01L 3/502715* (2013.01); *C12Q 1/6844* (2013.01); *G01N 33/52* (2013.01); *G01N 33/542* (2013.01); *B01L 2300/0819* (2013.01); *B01L 2400/0481* (2013.01); *G01N 21/645* (2013.01)

(58) Field of Classification Search
None
See application file for complete search history.

(56) References Cited

U.S. PATENT DOCUMENTS

| | | |
|---|---|---|
| 6,312,929 B1 | 11/2001 | McMillan |
| 10,246,737 B2 | 4/2019 | Ullrich |
| 2003/0082590 A1 | 5/2003 | Van Ness |

FOREIGN PATENT DOCUMENTS

| | | |
|---|---|---|
| EP | 1493822 A1 | 1/2005 |
| WO | 96/15270 A1 | 5/1996 |
| WO | 02/052030 A2 | 7/2002 |

OTHER PUBLICATIONS

International Search Report dated Jun. 22, 2015, issued in International Application No. PCT/EP2015/053759, 11 pages.
Ullrich et al., "Competitive reporter monitored amplification (CMA)—quantification of molecular targets by real time monitoring of competitive reporter hybridization." PLoS One. 2012;7(4):e35438.
Wittwer et al., "Real-time multiplex PCR assays." Methods. Dec. 2001;25(4):430-42.
Rosenstraus et al., "An internal control for routine diagnostic PCR: design, properties, and effect on clinical performance" J Clin Microbiol. Jan. 1998;36(1):191-7.

*Primary Examiner* — Kenneth R Horlick
(74) *Attorney, Agent, or Firm* — Casimir Jones, S.C.; Thomas A. Isenbarger

(57) ABSTRACT

The present invention relates to methods for determining the presence and/or amount of multiple nucleic acids in a sample.

20 Claims, 8 Drawing Sheets a)

b)

METHODS FOR DETECTING MULTIPLE NUCLEIC ACIDS IN A SAMPLE USING REPORTER COMPOUNDS AND BINDING MEMBERS THEREOF

This application is a continuation of U.S. patent application Ser. No. 15/116,185, filed Aug. 2, 2016, now U.S. Pat. No. 10,246,737, which issued on Apr. 2, 2019, and which claims the benefit under 35 U.S.C. § 371 to Int'l Pat. App. No. PCT/EP2015/053759, filed Feb. 23, 2015, which claims priority to United Kingdom Patent Application No. 1403076.1, filed Feb. 21, 2014, each of which is incorporated herein by reference in its entirety.

TECHNICAL FIELD

The present invention relates to methods for determining the presence and/or amount of multiple nucleic acids in a sample.

BACKGROUND

Real-time PCR enables continuous monitoring of labels during the generation of PCR products. Currently, available methods utilize either labeled probes or DNA intercalating dye to monitor the amplification of PCR products. For this purpose, single oligonucleotide probes containing a fluorophore and a quencher placed e.g. 10-30 bases apart may be used. Such a TaqMan probe can be hydrolyzed during the amplification due to the 5'-3' double strand-specific exonuclease activity of a Taq polymerase that separates the fluorophore from the quencher, resulting in fluorescence increase. Real-time PCR instruments are typically used which are equipped with fluorescence detectors and software capable of estimating the cycle threshold (Ct), which is the cycle at which fluorescence is greater than background fluorescence, for positive reactions.

However, well recognized difficulties in reproducing published tests due to variation in performance of PCR thermocyclers, inefficiency of different DNA polymerases, personnel and the presence of PCR inhibitors in the sample matrix can hamper implementation in laboratories, particularly those with extensive quality assurance programs. Lack of reproducible methods often forces testing laboratories to spend substantial resources on adaptation of the published tests. It is thus necessary to have internationally validated, open-formula PCR-based methods available in which the target gene, performance characteristics and validation criteria are known and which follow the ISO criteria for validation of alternative microbiological methods.

A major drawback of some published PCRs is that they do not contain an internal amplification control. In contrast to a (external) positive control, an internal amplification control is a non-target DNA sequence present in the very same sample, which is co-amplified simultaneously with the target sequence. In a PCR without an internal amplification control, a negative response (no band or signal) could mean that there was no target sequence present in the reaction. But, it could also mean that the reaction was inhibited, due to malfunction of thermal cycler, incorrect PCR mixture, poor DNA polymerase activity, or not least the presence of inhibitory substances in the sample matrix. In particular, after nucleic acid extraction, inhibitors may still be present from clinical samples (e.g. hemoglobin), environmental samples (e.g. humic and fulvic acids), and chemicals employed during nucleic acid extraction (e.g. ethanol detergents, or chaotropic agents). It is desirable to differentiate a true negative result from a false negative when PCR is affected by amplification inhibitors.

The reliability of diagnostic assays can be increased by the inclusion of an internal control nucleic acid that can indicate the presence and impact of PCR inhibitors. An internal positive control is usually amplified simultaneously in the presence of a target sequence using a labeled fluorophore that emits light at a different wavelength than the fluorophore used for the target sequence assay, with the two fluorophores detected in different channels by the real-time PCR instrument. The commonly used internal controls for PCR are plasmids that contain a sequence similar to that of the assay target except for probe region. A limited number of internal positive control molecules may be added to individual assay target and co-amplified with target nucleic acid. Thus, an internal positive control signal is evidence that the amplification reaction proceeded sufficiently to generate a positive signal from very small quantities of target nucleic acid.

However, some devices such as the LightCycler 1.2 and LightCycler 2 (Roche Applied Science, Indianapolis, Ind., USA), the Ruggedized Advanced Pathogen Identification Device (R.A.P.I.D.) instrument (Idaho Technology, Salt Lake City, Utah, USA), and handheld real-time PCR instruments are only equipped with one light source and associated emission channel.

To overcome this deficiency, P. Jothikumar et al., Biotechniques 46: 519-524 (2009) developed a design to create a triple-labeled probe as an internal positive control (IPC) that utilizes a combination of the fluorescence resonance energy transfer (FRET) and TaqMan techniques. The IPC probe, labeled with FAM and Cy5.5 fluorophores at the 5' end and Black Hole Quencher (BHQ) at the 3' end, enabled Cy5.5 emission through energy transfer from the FAM fluorophore. The second, target-specific TaqMan assay in the multiplex used an FAM and BHQ1-labeled probe at the 5' and 3' ends, respectively. Thus, one excitation source was used to generate two different fluorescence emissions (FAM and Cy5,5) that were measured in two separate channels by the real-time PCR instrument.

Rosenstraus et al., Journal of Clinical Microbiology, 36, 191-197 (1998) describe internal controls for routine diagnostic PCR, wherein the specific target and the internal control were detected in separate reactions using separate, target- and internal control-specific, oligonucleotide capture probes.

Umber et al., Applied and Environmental Microbiology, 67, 2837-2839 (2001) describe a real-time PCR method to quantitate viral DNA that includes duplex amplification, internal standardization, and two-color fluorescence detection without the need to generate an external standardization curve.

However, there is still a need in the art for suitable methods for detecting multiple nucleic acids, e.g. target nucleic acids and internal control nucleic acids, in a sample.

SUMMARY

The present invention relates to assays, e.g. assays for multiple analytes in a sample.

In one aspect, a method of determining the presence and/or amount of nucleic acids in a sample comprises:
(a) providing
an amount of a first nucleic acid;
an amount of a second nucleic acid;
an amount of a FRET compound capable of forming complexes with the first nucleic acid, wherein the FRET compound comprises a binding portion specific to a region of the first nucleic acid, and a first detectable label that has, in an uncomplexed state, a first detectable characteristic and, in a complexed state, a second detectable characteristic a second detectable characteristic which differs from the first detectable characteristic;

an amount of a reporter compound capable of forming complexes with the second nucleic acid, wherein each reporter compound comprises a binding portion specific to a region of the second nucleic acid and a second detectable label; and a binding member capable of capturing the reporter compound;

wherein forming of complexes of the second nucleic acid with the reporter compound inhibits capturing of the reporter compound by the binding member;

(b) forming complexes each comprising a first nucleic acid and a FRET compound;

(c) forming complexes of a subset of the amount of reporter compound with a second nucleic acid;

(d) capturing a remaining subset of the amount of reporter compound not in complex with a second nucleic acid on the binding member;

(e) determining a value indicative for the presence and/or amount of first nucleic acid captured by FRET compounds; and (f) determining a value indicative for the presence and/or amount of reporter compound captured on the binding member.

The method may further comprising determining a value indicative for the presence and/or amount of second nucleic acid based on the value indicative for the presence and/or amount of reporter compound captured on the binding member.

In some embodiments, the first and/or second detectable label of the FRET compound is a fluorescent label. In particular, both the first detectable label and the second detectable label emit in a wavelength range of from 300 nm to 850 nm, e.g. 450 nm to 750 nm or 550 to 650 nm. In an exemplary embodiment, both the first detectable label and the second detectable label are identical.

The value indicative for the presence and/or amount of first nucleic acid captured by FRET compounds may be determined in a complexed state of the FRET compounds.

Further, the first nucleic acid may be an analyte, e.g. a first analyte. The second nucleic acid may be selected from the group consisting of an analyte, e.g. a second analyte, and a control nucleic acid. The control nucleic acid may be selected from the group consisting of a positive amplification control and a negative amplification control.

In some embodiments, the first nucleic acid may be present in an amount of less than 100 copies per sample. In addition or alternatively, the second nucleic acid may be present in an amount of 100 copies or more per sample.

Further, the steps of (i) forming complexes each comprising a first nucleic acid and a FRET compound, (ii) forming complexes of a subset of the amount of reporter compound with at least a subset of the amount of second nucleic acid and (iii) capturing a remaining subset of the amount of reporter compound not in complex with a second nucleic acid on the binding member may be performed concomitantly.

According to another embodiment, the method further comprises subjecting the first and/or second nucleic acid to amplification. Optionally, e.g. in case of subjecting the first and/or second nucleic acid to a cyclic amplification reaction, amplification of the first and second nucleic acid is initiated prior to the step of forming complexes of a subset of the amount of reporter compound with at least a subset of the amount of second nucleic acid. Further, e.g. in case of subjecting the first and/or second nucleic acid to an isothermal amplification reaction, the steps of (i) forming complexes each comprising a first nucleic acid and a FRET compound, (ii) forming complexes of a subset of the amount of reporter compound with at least a subset of the amount of second nucleic acid, (iii) capturing a remaining subset of the amount of reporter compound not in complex with a second nucleic acid on the binding member, and (iv) subjecting the first and/or second nucleic acid to amplification may be performed concomitantly.

Further, the binding member may comprise one or more different reporter specific capture compounds being capable of capturing a reporter compound on the binding member. The reporter specific capture compounds may be oligonucleotides. In particular, the different reporter specific capture compounds, e.g. oligonucleotides, can be arranged on different locations with respect to the binding member.

The reporter compounds may be captured on the binding member by forming complexes with the reporter specific capture compounds.

According to specific embodiments, at least a part of an interaction site of the reporter compound being capable of forming a complex with a second nucleic acid is also capable of forming a complex with a reporter specific capture compound. In particular, the reporter specific capture compounds and the second nucleic acid may compete for forming a complex with the reporter compound.

In some embodiments, the value indicative for the presence and/or amount of first nucleic acid captured by FRET compounds and/or the value indicative for the presence and/or amount of reporter compound captured on the binding member is determined in a reaction chamber comprising the binding member and a cover element. The cover element may be configured to be at least partially deformable such that the reaction chamber has a relaxed state interior volume and a compressed state interior volume.

In a specific embodiment, the value indicative for the presence and/or amount of first nucleic acid captured by FRET compounds is determined in the reaction chamber having a relaxed state interior volume. Further, the value indicative for the presence and/or amount of reporter compound captured on the binding member can be determined in the reaction chamber having a compressed state interior volume. For example, the value indicative for the presence and/or amount of first nucleic acid captured by FRET compounds is determined in the reaction chamber having a relaxed state interior volume and the value indicative for the presence and/or amount of reporter compound captured on the binding member is determined in the reaction chamber having a compressed state interior volume.

Further, the value indicative for the presence and/or amount of first nucleic acid captured by FRET compounds and the value indicative for the presence and/or amount of reporter compound captured on the binding member can be determined consecutively or concomitantly.

In another embodiment, the reporter compounds are oligonucleotides.

The method may further comprise subjecting the first and/or second nucleic acids to reverse transcription prior to subjecting them to amplification.

In a specific embodiment, the method of determining the presence and/or amount of nucleic acids in a sample comprises:

providing an amount of a first nucleic acid; an amount of a second nucleic acid; an amount of a FRET compound capable of forming complexes with the first nucleic acid, wherein the FRET compound comprises a binding portion specific to a region of the first nucleic acid, and a first detectable label that has, in an uncomplexed state, a first detectable characteristic and, in a complexed state, a second detectable characteristic a second detectable characteristic which differs from the first detectable characteristic; an amount of a reporter compound capable of forming complexes with the second nucleic acid, wherein each reporter compound comprises a binding portion specific to a region of the second nucleic acid and a second detectable label; and a binding member capable of capturing the reporter compound;

wherein forming of complexes of the second nucleic acid with the reporter compound inhibits capturing of the reporter compound by the binding member; subjecting the first and/or second nucleic acid to amplification;

forming complexes each comprising a first nucleic acid and a FRET compound;

forming complexes of a subset of the amount of reporter compound with a second nucleic acid;

capturing a remaining subset of the amount of reporter compound not in complex with a second nucleic acid on the binding member;

determining a value indicative for the presence and/or amount of first nucleic acid captured by FRET compounds; and determining a value indicative for the presence and/or amount of reporter compound captured on the binding member.

In some embodiments, the amplification comprises a step of denaturing double stranded nucleic acids, wherein the double stranded nucleic acids comprise complexes of reporter compounds with second nucleic acids, complexes of reporter compounds with reporter specific capture compounds, double strands of reporter compounds and double strands of first and/or second nucleic acids. Alternatively or in addition, the amplification may comprise a step of annealing primer compounds to first and/or second nucleic acids, wherein optionally the annealing step is performed concomitantly with the step of forming complexes of a subset of the amount of reporter compound with at least a subset of the amount of second nucleic acid and/or the step of capturing a remaining subset of the amount of reporter compound not in complex with a second nucleic acid on the binding member.

In a specific embodiment, the amplification is an isothermal amplification method. For example, the isothermal amplification method is an isothermal NEAR.

In such an embodiment, the method of determining the presence and/or amount of nucleic acids in a sample may comprise:

providing an amount of a first nucleic acid; an amount of a second nucleic acid; an amount of a FRET compound capable of forming complexes with the first nucleic acid, wherein the FRET compound comprises a binding portion specific to a region of the first nucleic acid, and a first detectable label that has, in an uncomplexed state, a first detectable characteristic and, in a complexed state, a second detectable characteristic a second detectable characteristic which differs from the first detectable characteristic; an amount of a reporter compound capable of forming complexes with the second nucleic acid, wherein each reporter compound comprises a binding portion specific to a region of the second nucleic acid and a second detectable label; and a binding member capable of capturing the reporter compound;

wherein forming of complexes of the second nucleic acid with the reporter compound inhibits capturing of the reporter compound by the binding member;

subjecting the first and/or second nucleic acid to an isothermal amplification, e.g. an isothermal NEAR;

forming complexes each comprising a first nucleic acid and a FRET compound;

forming complexes of a subset of the amount of reporter compound with a second nucleic acid;

capturing a remaining subset of the amount of reporter compound not in complex with a second nucleic acid on the binding member;

determining a value indicative for the presence and/or amount of first nucleic acid captured by FRET compounds; and determining a value indicative for the presence and/or amount of reporter compound captured on the binding member;

wherein optionally the steps of (i) forming complexes each comprising a first nucleic acid and a FRET compound, (ii) forming complexes of a subset of the amount of reporter compound with at least a subset of the amount of second nucleic acid, (iii) capturing a remaining subset of the amount of reporter compound not in complex with a second nucleic acid on the binding member, and (iv) subjecting the first and/or second nucleic acid to amplification may be performed concomitantly.

In other embodiments, the amplification is a cyclic amplification, wherein the cyclic amplification optionally is a PCR, wherein performing the PCR optionally comprises using a polymerase having exonuclease activity. For example, the value indicative for the presence and/or amount of reporter compound captured on the binding member is determined after at least one cycle of the cyclic amplification, and optionally after each cycle of the cyclic amplification. The value indicative for the presence and/or amount of first and/or second nucleic acid may then be determined each time after determining the value indicative for the presence and/or amount of reporter compound captured on the binding member.

In such an embodiment, the method of determining the presence and/or amount of nucleic acids in a sample comprises:

providing an amount of a first nucleic acid; an amount of a second nucleic acid; an amount of a FRET compound capable of forming complexes with the first nucleic acid, wherein the FRET compound comprises a binding portion specific to a region of the first nucleic acid, and a first detectable label that has, in an uncomplexed state, a first detectable characteristic and, in a complexed state, a second detectable characteristic a second detectable characteristic which differs from the first detectable characteristic; an amount of a reporter compound capable of forming complexes with the second nucleic acid, wherein each reporter compound comprises a binding portion specific to a region of the second nucleic acid and a second detectable label; and a binding member capable of capturing the reporter compound; wherein forming of complexes of the second nucleic acid with the reporter compound inhibits capturing of the reporter compound by the binding member;

subjecting the first and/or second nucleic acid to a cyclic amplification, e.g. a PCR;

forming complexes each comprising a first nucleic acid and a FRET compound;

forming complexes of a subset of the amount of reporter compound with a second nucleic acid;

capturing a remaining subset of the amount of reporter compound not in complex with a second nucleic acid on the binding member;

determining a value indicative for the presence and/or amount of first nucleic acid captured by FRET compounds; and determining a value indicative for the presence and/or amount of reporter compound captured on the binding member, wherein optionally amplification of the first and second nucleic acid is initiated prior to the step of forming complexes of a subset of the amount of reporter compound with at least a subset of the amount of second nucleic acid.

In the methods described above, the value indicative for the presence and/or amount of a second nucleic acid may be determined based on a calibration curve correlating the value indicative for the presence and/or amount of reporter compound with the value indicative for the presence and/or amount of second nucleic acid.

In a specific embodiment, the method of determining the presence and/or amount of nucleic acids in a sample comprises:

providing in a reaction chamber an amount of a first nucleic acid; an amount of a second nucleic acid; an amount of a FRET compound capable of forming complexes with the first nucleic acid, wherein the FRET compound comprises a binding portion specific to a region of the first nucleic acid, and a first detectable label that has, in an uncomplexed state, a first detectable characteristic and, in a complexed state, a second detectable characteristic; and an amount of a reporter compound capable of forming complexes with the second nucleic acid, wherein each reporter compound comprises a binding portion specific to a region of the second nucleic acid and a second detectable label; wherein the reaction chamber comprises a binding member capable of capturing the reporter compound, wherein forming of complexes of the second nucleic acid with the reporter compound inhibits capturing of the reporter compound by the binding member, and a cover element which is configured to be at least partially deformable;

subjecting the first and/or second nucleic acid to amplification, e.g. isothermal or cyclic amplification;

forming complexes each comprising a first nucleic acid and a FRET compound;

forming complexes of a subset of the amount of reporter compound with a second nucleic acid;

capturing a remaining subset of the amount of reporter compound not in complex with a second nucleic acid on the binding member;

determining a value indicative for the presence and/or amount of first nucleic acid captured by FRET compounds in solution; and determining a value indicative for the presence and/or amount of reporter compound captured on the binding member, and, based on the value indicative for the presence and/or amount of reporter compound captured on the binding member, determining a value indicative for the presence and/or amount of second nucleic acid.

In another specific embodiment, the method of determining the presence and/or amount of nucleic acids in a sample comprises:

providing in a reaction chamber an amount of a first nucleic acid; an amount of a second nucleic acid; an amount of a FRET compound capable of forming complexes with the first nucleic acid, wherein the FRET compound comprises a binding portion specific to a region of the first nucleic acid, and a first detectable label that has, in an uncomplexed state, a first detectable characteristic and, in a complexed state, a second detectable characteristic; and an amount of a reporter compound capable of forming complexes with the second nucleic acid, wherein each reporter compound comprises a binding portion specific to a region of the second nucleic acid and a second detectable label; wherein the reaction chamber comprises a binding member capable of capturing the reporter compound, wherein forming of complexes of the second nucleic acid with the reporter compound inhibits capturing of the reporter compound by the binding member, and a cover element which is configured to be at least partially deformable such that the reaction chamber has a relaxed state interior volume and a compressed state interior volume;

subjecting the first and/or second nucleic acid to amplification, e.g. isothermal or cyclic amplification;

forming complexes each comprising a first nucleic acid and a FRET compound;

forming complexes of a subset of the amount of reporter compound with a second nucleic acid;

capturing a remaining subset of the amount of reporter compound not in complex with a second nucleic acid on the binding member;

determining a value indicative for the presence and/or amount of first nucleic acid captured by FRET compounds in the reaction chamber having a relaxed state interior volume; and determining a value indicative for the presence and/or amount of reporter compound captured on the binding member in the reaction chamber having a compressed state interior volume, and, based on the value indicative for the presence and/or amount of reporter compound captured on the binding member, determining a value indicative for the presence and/or amount of second nucleic acid.

In another specific embodiment, the method of determining the presence and/or amount of nucleic acids in a sample comprises:

providing in a reaction chamber an amount of a first nucleic acid; an amount of a second nucleic acid; an amount of a FRET compound capable of forming complexes with the first nucleic acid, wherein the FRET compound comprises a binding portion specific to a region of the first nucleic acid, and a first detectable label that has, in an uncomplexed state, a first detectable characteristic and, in a complexed state, a second detectable characteristic; and an amount of a reporter compound capable of forming complexes with the second nucleic acid, wherein each reporter compound comprises a binding portion specific to a region of the second nucleic acid and a second detectable label; wherein the reaction chamber comprises a binding member capable of capturing the reporter compound, wherein forming of complexes of the second nucleic acid with the reporter compound inhibits capturing of the reporter compound by the binding member, and a cover element which is configured to be at least partially deformable such that the reaction chamber has a relaxed state interior volume and a compressed state interior volume;

subjecting the first and/or second nucleic acid to amplification, e.g. isothermal or cyclic amplification;

forming complexes each comprising a first nucleic acid and a FRET compound;

forming complexes of a subset of the amount of reporter compound with a second nucleic acid;

capturing a remaining subset of the amount of reporter compound not in complex with a second nucleic acid on the binding member;

determining a value indicative for the presence and/or amount of first nucleic acid captured by FRET compounds in solution in the reaction chamber having a relaxed state interior volume; and determining a value indicative for the presence and/or amount of reporter compound captured on the binding member in the reaction chamber having a compressed state interior volume, and, based on the value indicative for the presence and/or amount of reporter compound captured on the binding member, determining a value indicative for the presence and/or amount of second nucleic acid.

In another specific embodiment, the method of determining the presence and/or amount of nucleic acids in a sample comprises:

introducing into a reaction chamber an amount of a first nucleic acid; an amount of a second nucleic acid; an amount of a FRET compound capable of forming complexes with the first nucleic acid, wherein the FRET compound comprises a binding portion specific to a region of the first nucleic acid, and a first detectable label that has, in an uncomplexed state, a first detectable characteristic and, in a complexed state, a second detectable characteristic; and an amount of a reporter compound capable of forming complexes with the second nucleic acid, wherein each reporter compound comprises a binding portion specific to a region of the second nucleic acid and a second detectable label; wherein the reaction chamber comprises a first surface, a second surface and a binding member capable of capturing the reporter compound, wherein the distance between the first and the second surface can be varied such that the reaction chamber has a relaxed state interior volume and a compressed state interior volume and wherein forming of complexes of the second nucleic acid with the reporter compound inhibits capturing of the reporter compound by the binding member;

subjecting the first and/or second nucleic acid to amplification, e.g. isothermal or cyclic amplification;

forming complexes each comprising a first nucleic acid and a FRET compound;

forming complexes of a subset of the amount of reporter compound with a second nucleic acid;

capturing a remaining subset of the amount of reporter compound not in complex with a second nucleic acid on the binding member;

determining a value indicative for the presence and/or amount of first nucleic acid captured by FRET compounds in solution in the reaction chamber having a relaxed state interior volume; and determining a value indicative for the presence and/or amount of reporter compound captured on the binding member in the reaction chamber having a compressed state interior volume, and, based on the value indicative for the presence and/or amount of reporter compound captured on the binding member, determining a value indicative for the presence and/or amount of second nucleic acid.

The aspects defined above and further aspects are apparent from the examples of embodiment to be described hereinafter and are explained with reference to these examples of embodiment.

BRIEF DESCRIPTION OF THE DRAWINGS

Exemplary embodiments will be described in more detail hereinafter but to which the invention is not limited. The illustration in the drawings is schematically.

DETAILED DESCRIPTION

Figure 1:
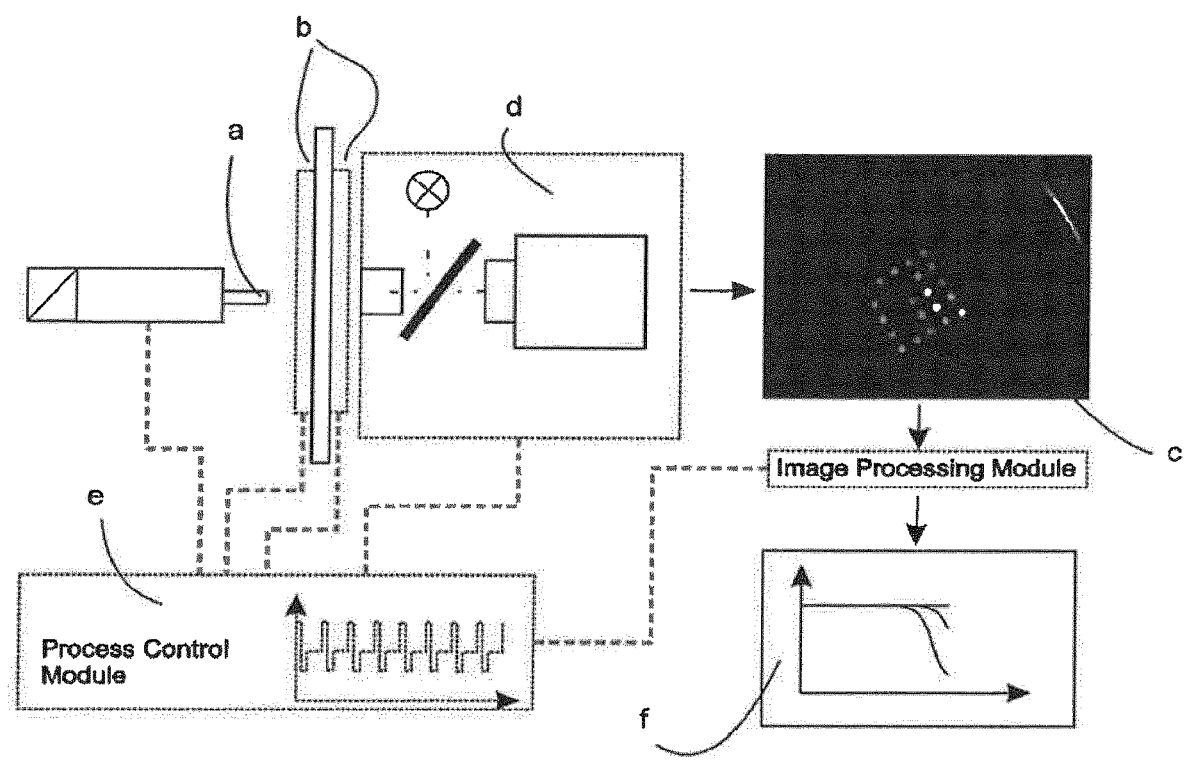
FIG. 1 is a schematic drawing of an exemplary test device as described herein.

Where the term "comprise" or "comprising" is used in the present description and claims, it does not exclude other elements or steps. For the purpose of the present disclosure, the term "consisting of" is considered to be an optional embodiment of the term "comprising of". If hereinafter a group is defined to comprise at least a certain number of embodiments, this is also to be understood to disclose a group which optionally consists only of these embodiments.

Where an indefinite or a definite article is used when referring to a singular noun, e.g. "a" or "an", "the", this includes a plural form of that noun unless specifically stated. For example, when a first or second nucleic acid is mentioned, this is also to be understood as first or second nucleic acids. Vice versa, when the plural form of a noun is used it refers also to the singular form.

Furthermore, the terms first, second, third or (a), (b), (c) and the like in the description and in the claims are used for distinguishing between similar elements and not necessarily for describing a sequential or chronological order. It is to be understood that the terms so used are interchangeable under appropriate circumstances and that the embodiments described herein are capable of operation in other sequences than described or illustrated herein.

Further definitions of the terms will be given below in the context of which the terms are used.

Analysis of biological samples may include determining whether one or more nucleic acids (for instance, a DNA, RNA, mRNA, or rRNA) are present in the sample. For example, one may analyze a sample to determine whether a nucleic acid indicative of the presence of a particular pathogen is present.

According to an exemplary aspect, a method of determining the presence and/or amount of multiple nucleic acids in a sample comprises (a) providing
   an amount of a first nucleic acid;
   an amount of a second nucleic acid;
   an amount of a FRET compound capable of forming complexes with the first nucleic acid, wherein the FRET compound comprises a binding portion specific to a region of the first nucleic acid, and a first detectable label that has, in an uncomplexed state, a first detectable characteristic and, in a complexed state, a second detectable characteristic;

an amount of a reporter compound capable of forming complexes with the second nucleic acid, wherein each reporter compound comprises a binding portion specific to a region of the second nucleic acid and a second detectable label; and a binding member capable of capturing the reporter compound;

wherein forming of complexes of the second nucleic acid with the reporter compound inhibits capturing of the reporter compound by the binding member;

(b) forming complexes each comprising a first nucleic acid and a FRET compound;

(c) forming complexes of a subset of the amount of reporter compound with a second nucleic acid;

(d) capturing a remaining subset of the amount of reporter compound not in complex with a second nucleic acid on the binding member;

(e) determining a value indicative for the presence and/or amount of first nucleic acid captured by FRET compounds; and (f) determining a value indicative for the presence and/or amount of reporter compound captured on the binding member.

In particular, the first nucleic acid may be detected via determining a value indicative for the presence and/or amount of first nucleic acid captured by FRET compounds in solution, whereas the second nucleic acid, e.g. a control nucleic acid, can be detected via determining a value indicative for the presence and/or amount of reporter compound captured on the binding member. This may avoid the use of different chromophores for the detection of multiple nucleic acids in a solution. Further, by detecting values indicative for the presence and/or amount of controls via surface-bound substrates or probes, it is possible to implement controls not associated with amplification, such as enzyme controls, and thereby avoid the synthesis of a corresponding mimic amplicon.

The term "nucleic acid" or "target nucleic acid" or "target analyte", as used herein, denotes any nucleic acid molecule that can be detected by using the method (e.g. target nucleic acids that are capable of forming complexes with a FRET compound, or target nucleic acids or control nucleic acids that are capable of forming complexes with a reporter compound; see below). Examples of such nucleic acid molecules include naturally occurring nucleic acids such as deoxyribonucleic acid (DNA) or ribonucleic acid (RNA) as well as artificially designed nucleic acids, e.g., nucleic acid analogs such as inter alia peptide nucleic acids (PNA) or locked nucleic acids (LNA), that are chemically synthesized or generated by means of recombinant gene technology (see, for example, Sambrook, J. et al. (1989) *Molecular, Cloning: A Laboratory Manual,* 2nd ed., Cold Spring Harbor Laboratory Press, Cold Spring Harbor, N.Y.). Specific examples of naturally occurring nucleic acids include DNA sequences such as genomic DNA or cDNA molecules as well as RNA sequences such as hnRNA, mRNA or rRNA molecules or the reverse complement nucleic acid sequences thereof. Such nucleic acids can be of any length and can be either single-stranded or double-stranded molecules. Typically, target nucleic acids are 10 to 10000 nucleotides in length, e.g., 20 to 2000 nucleotides, 30 to 1000 nucleotides or 50 to 500 nucleotides. As used herein, the term "nucleotide" is to be understood as referring to both ribonucleotides and deoxyribonucleotides (i.e. RNA and DNA molecules).

The target analyte or target nucleic acid may be a nucleic acid associated with bacterial or viral infections.

A nucleic acid associated with bacterial infections may denote any nucleic acid molecule of bacterial origin (e.g. whose nucleotide sequence is identical or complementary to a corresponding sequence within the bacterium genome) that is present in a liquid sample to be analyzed that has been infected by one or more bacterium species. Examples of bacteria that cause bacterial infections include inter alia *Mycobacterium tuberculosis, Streptococcus, Pseudomonas, Shigella, Campylobacter, Staphylococcus aureus, Escherichia coli,* and *Salmonella.* One of the bacterial diseases with highest disease burden is tuberculosis, caused by the bacterium *Mycobacterium tuberculosis* which kills about 2 million people a year, mostly in sub-Saharan Africa. Thus, in some embodiments, the target nucleic acid or target analyte to be detected is associated with infections caused by *Mycobacterium tuberculosis.*

A nucleic acid associated with viral infections may denote any nucleic acid molecule of viral origin (e.g. whose nucleotide sequence is identical or complementary to a corresponding sequence within the virus genome) that is present in a liquid sample to be analyzed that has been infected by one or more virus species. The viruses infecting the host, from which the liquid sample is obtained, may be any DNA virus (i.e. a virus having a DNA genome) or RNA virus (i.e. a virus having a RNA genome) (reviewed, e.g., in: Büchen-Osmond, C. (2003). *Taxonomy and Classification of Viruses.* In: Manual of Clinical Microbiology, 8th ed., vol. 2, p. 1217-1226, ASM Press, Washington D.C.). Examples of DNA viruses include inter alia the families of Papovaviridae (e.g. papillomavirus), Adenoviridae (e.g. adenovirus), and Herpesviridae (e.g. Epstein-Barr virus, cytomegalovirus). Examples of RNA viruses include inter alia the families of Picornaviridae (e.g. poliovirus, rhinovirus) Flaviviridae (e.g. hepatitis C virus), Filoviridae (e.g. Marburg virus, ebolavirus), and Retroviridae (e.g. human immunodeficiency virus (HIV)). In some embodiments, target nucleic acids to be detected are associated with infections caused by members of the Retroviridae, particularly they are associated with HIV infections. The term "HIV", as used herein, refers to both the HIV-1 and HIV-2 species and to any subtypes derived thereof.

Since many DNA viruses as well as the Retroviridae (notably, the replication of the Retroviridae generally requires reverse transcription of the RNA virus genome into DNA), can integrate their genetic information into the host cell's genome in form of a latent pro-virus, the term "nucleic acids associated with viral infections" does not only refer to nucleic acids originating from free and from cell-associated viruses but also to pro-viral DNA molecules being integrated into the host's genome, reverse transcribed viral DNA molecules (i.e. the "intermediates" of viral replication), and transcripts derived from pro-viral DNA (i.e. RNA molecules obtained by transcription of the host DNA genome).

Typically, the target nucleic acids are not subjected in isolated form to the method disclosed herein but in form of a sample that is supposed to comprise one or more species of target nucleic acids. The term "one or more species", as used herein, refers to one or more different types of nucleic acids such as molecules having different nucleotide sequences and/or molecules descending from different origins (e.g., nucleic acids derived from different pathogens infecting a host cell).

Typically, the first nucleic acid as used herein is a target analyte or target nucleic acid as described above.

In some embodiments, the second nucleic acid may be a target analyte as described above. In addition or alternatively, the second nucleic acid may be a control nucleic acid. Control nucleic acids may include positive and negative amplification controls and are described in more detail below.

If both the first and second nucleic acid are a target analyte, the second nucleic acid typically differs from the first nucleic acid, e.g., is a different type of nucleic acid such as a molecule having a different nucleotide sequence and/or a molecule descending from a different origin (e.g., a nucleic acid derived from a different pathogen infecting a host cell). In this embodiment, the first nucleic acid may also be referred to as a first target analyte and the second nucleic acid may also be referred to as a second target analyte. For example, the first target analyte is associated with HIV infections and the second target analyte is associated with HCV infections.

Typically, amplicons of the first and/or second nucleic acid, e.g. amplicons of a target analyte and/or a control nucleic acid, have a length of 10 to 300 nucleotides, for example 15 to 250 nucleotides, 30 to 200 nucleotides or 50 to 100 nucleotides.

Further, a "second nucleic acid" as used herein may include more than one nucleic acid type such as one or more target analytes differing from the first target analyte (e.g. a second, third, fourth, fifth, etc. target analyte) and one or more control nucleic acids (e.g. positive and negative amplification control nucleic acids).

The term "sample", as used herein, refers to any liquid, which is to be analyzed by using the methods described herein, and which is supposed to comprise one or more species of target nucleic acids to be detected. Thus, a sample may comprise purified nucleic acid preparations dissolved in water or a suitable buffer (e.g. Tris/EDTA) as well as various biological samples. Examples of liquid samples that can be analyzed using the methods described herein include inter alia organic and inorganic chemical solutions, drinking water, sewage, human and non-human body fluids such as whole blood, plasma, serum, urine, sputum, *salvia* or cerebrospinal fluid, cellular extracts from animals, plants or tissue cultures, prokaryotic and eukaryotic cell suspensions, phage preparations and the like.

In a specific embodiment, e.g. in a case where the target nucleic acid is associated with a bacterial infection such as such as an infection caused by *Mycobacterium tuberculosis*, the liquid sample that can be analyzed using the methods described herein is a human sputum sample or a human urine sample.

In another specific embodiment, e.g. in a case where the target nucleic acid is associated with a viral infection such as an infection caused by HIV or hepatitis C virus, the liquid sample that can be analyzed using the methods described herein is a human whole blood sample or a human plasma sample.

The term "whole blood", as used herein, refers to blood with all its constituents. In other words, whole blood comprises both blood cells such as erythrocytes, leukocytes, and thrombocytes, and blood plasma in which the blood cells are suspended.

The sample may further comprise one or more additional agents such as diluents, solvents or buffers that may result from an optional purification and/or processing of the sample prior to subjecting it to the methods described herein. However, in some embodiments, the sample analyzed is an untreated sample such as an untreated whole blood sample. The term "untreated", as used herein, is to be understood that after collecting the sample (e.g., by blood withdrawal from a patient) and before subjecting it to the methods described herein in a test device as described below no further sample processing (e.g., fractionation methods, drying/reconstitution, and the like) occurs.

A typical nucleic acid detection method involving such untreated samples is described below.

The volume of the fluid sample to be analyzed may be in the range of 1 µl to 30 ml, such as 5 µl to 20 ml or 10 µl to 10 ml.

In particular, the volume of a urine or sputum sample to be analyzed may be in the range of 1 ml to 30 ml, typically in the range of 1 ml to 25 ml or 1 ml to 20 ml or 1 ml to 15 ml or 1 ml to 10 ml. In particular embodiments, the volume of urine or sputum sample is in the range of 5 ml to 15 ml such as about 10 ml. However, sample volumes exceeding 30 ml are within the scope of the disclosure as well.

Further, the volume of a whole blood or plasma sample to be analyzed may be in the range of 1 µl to 50 µl, typically in the range of 1 µl to 45 µl or 1 µl to 40 µl or 1 µl to 30 µl or 1 µl to 25 µl or 1 µl to 20 µl or 1 µl to 15 µl. In particular embodiments, the volume of the fluid sample such as a human whole blood sample is in the range of 1 µl to 10 µl. However, in case whole blood samples are analyzed sample volumes exceeding 50 µl are within the scope of the disclosure as well.

The term "reporter molecule" or "reporter compound", as used herein, may denote any molecule that is capable of forming complexes with one or more second nucleic acids and that can be captured on a support member, e.g. a binding member, wherein the forming of complexes with the second nucleic acids inhibits the capturing of the reporter compound on the support member, e.g. the binding member. Thereby, the term "capable of forming complexes", as used herein, refers to any interaction between a reporter compound and a second nucleic acid. In particular, the term may denote the binding of the molecules to each other that may be accomplished via a common or different binding regions comprised in the reporter molecule that mediate the interaction with the target (such as via Watson-Crick base pairing between complementary nucleotide sequences). Typically, the interaction is reversible. Analogously, the term "being captured on a support member" or "being captured on the binding member" also denotes any direct or indirect (for example, via capture molecules; see below) interaction of a reporter molecule with a given binding member. This interaction is generally reversible as well.

In general, the reporter compounds may be nucleic acid molecules (i.e. RNA or DNA molecules as described above) having a length of 10 to 100 nucleotides, for example to 50 nucleotides, 15 to 40 nucleotides or 20 to 30 nucleotides. Usually, the reporter molecules are single-stranded nucleic acid molecules or oligonucleotides. The reporter compound is configured such that the binding of such a reporter compound to a second nucleic acid to be detected inhibits the capturing of the reporter compound on the binding member. The nucleic acid reporter molecules may comprise at least one specific binding region (herein also referred to as "interaction site") that is not only capable of interacting with the second nucleic acid (e.g., by binding to an at least partially complementary sequence region of the second nucleic acid, thus allowing, e.g., Watson-Crick base-pairing between the reporter molecule and the second nucleic acid to be detected), but also of being captured on the binding member. Typically, the specific binding region comprised in the reporter compound is at least 12 nucleotides in length, e.g. at least 15 nucleotides, at least 18 nucleotides or at least 22 nucleotides. In particular embodiments, the nucleotide sequence of the binding portion of the reporter compound is complementary to the corresponding nucleotide sequence of the second nucleic acid.

One or more species of reporter molecules may be employed, e.g. depending on the number of different types of nucleic acids, e.g. second nucleic acids, which are to be determined. The term "one or more species" denotes one or more different types of reporter compounds such as one or more nucleic acid molecules having different nucleotide sequences.

A "binding member" as used herein may refer to any solid matrix on which reporter molecules, can be captured. Examples of such matrices comprise inter alia synthetic particles such as magnetic beads (e.g., paramagnetic polystyrol beads, also known as Dynabeads®) and latex beads. A "binding member", as used herein, may e.g. refer to any solid matrix, on which the reporter compounds can be captured either directly (e.g., via an anchor group comprised in the reporter compound) or in an indirect manner via one or more species of reporter specific capture compounds capable of capturing a reporter compound to the binding member by covalent or non-covalent interactions. Examples of binding members that can be used comprise inter alia the substrates of array elements (e.g., microscope slides, wafers or ceramic materials).

The term "reporter specific capture compound" or "reporter specific capture molecule", as used herein, denotes any compound or molecule being e.g. attached to or immobilized on the binding member that shows a specific binding behavior and/or a characteristic reactivity, which makes it suitable for the formation of complexes with a reporter compound (i.e. the binding to the reporter compound). Nucleic acids or oligonucleotides are typically used as reporter specific capture molecules. Examples of nucleic acids that can be used as reporter specific capture molecules include naturally occurring nucleic acids such as deoxyribonucleic acid (DNA) or ribonucleic acid (RNA) as well as nucleic acid analogs such as inter alia peptide nucleic acids (PNA) or locked nucleic acids (LNA). Specific examples of naturally occurring nucleic acids include DNA sequences such as genomic DNA or cDNA molecules as well as RNA sequences such as hnRNA, mRNA or rRNA molecules or the reverse complement nucleic acid sequences thereof. Such nucleic acids can be of any length and can be either single-stranded or double-stranded molecules. Typically, reporter specific capture compounds are single-stranded oligonucleotides having a length of 10 to 100 nucleotides, e.g. of 15 to 50 nucleotides or 20 to 30 nucleotides.

The reporter specific capture compounds may comprise at least one specific sequence region (i.e. the binding region), which is configured to bind a reporter compound, for example, to interact with a complementary sequence region of a reporter molecule via base-pairing between the reporter specific capture molecules and the nucleic acid to be detected. Typically, the specific binding region is at least 12 nucleotides in length, e.g. at least 15 nucleotides, at least 18 nucleotides or at least 22 nucleotides. In particular embodiments, the nucleotide sequence of the binding region of the reporter specific capture compound is complementary to the corresponding nucleotide sequence of the reporter compound.

In some embodiments, at least a part of an interaction site of the reporter compound being capable of forming a complex with a second nucleic acid is also capable of forming a complex with a reporter specific capture compound. In particular, the reporter specific capture molecules and the second nucleic acids compete for forming a complex with the reporter compound, e.g., the respective binding regions comprised in the reporter specific capture molecules and the second nucleic acids recognize the same or at least similar corresponding sequence(s) of a reporter molecule. The term "similar sequences", as used herein, denotes sequences that differ only in one or more single nucleotide mismatches (i.e. non-complementary pairs of nucleotides) or by one or more single nucleotide additions, insertions or deletions (i.e. additional or lacking nucleotide residues). Thus, the respective binding regions comprised in the reporter specific capture molecules and the second nucleic acids may be at least partially identical. The term "partially identical", as used herein, denotes sequences differing only in one or more single nucleotides, as described above, or sequences having overlapping binding sites, i.e. sequences sharing a common nucleotide sequence but differ in at least one other part of the sequence region. However, it is also possible that the respective binding regions comprised in the reporter specific capture molecules and the target nucleic acids recognize different, non-overlapping (e.g., adjacent) sequences of a reporter molecule but binding of either the reporter specific capture molecule or the target nucleic acid to the reporter molecule sterically interferes with the binding of the other one.

In some embodiments, the chemical equilibrium between the steps of forming of complexes of reporter compound and second nucleic acid on the one hand and capturing of reporter compound on the binding member (e.g. by forming complexes with a reporter specific capture molecule) on the other hand may be influenced by varying the degree of similarity and/or partial identity of the sequences of the reporter specific capture molecule (with respect to the reporter compound sequences) and the reporter compound (with respect to the second nucleic acid), respectively.

For instance, the reporter specific capture molecule sequences may be selected such that the binding region with respect to the reporter compound sequence is shorter or longer than that of the binding region of the reporter compound sequence with respect to the second nucleic acid sequence. In this way, the binding affinity of the reporter compound with respect to the second nucleic acid compared to that of the reporter compound with respect to the reporter specific capture molecule may be increased or decreased.

One or more species of reporter specific capture molecules may be employed. The term "one or more species" denotes one or more different types of reporter specific capture molecules such as one or more nucleic acid molecules having different nucleotide sequences. More than one species of reporter specific capture molecule concomitantly used are also referred to as "library". Such libraries comprise at least two but may also comprise many more different molecules, e.g. at least 10 different species, at least 20 different species, at least 50 different species and so forth. The different reporter specific capture compounds or libraries may also be arranged on different locations with respect to the binding member. For example, they may be present in form of arrays or any other spatial arrangement.

The term "array" (also referred to as "microarray"), as used herein, refers to a defined spatial arrangement (layout) of capture molecules such as reporter specific capture molecules on a binding member, also referred to as "substrate", wherein the position of each species of molecule within the array is determined separately. Typically, the microarray comprises defined sites or predetermined regions, i.e. socalled "array elements" or "spots", which may be arranged in a particular pattern, wherein each array element typically comprises only one species of reporter specific capture molecules. The arrangement of the reporter specific capture molecules on the binding member can be generated by means of covalent or non-covalent interactions.

FRET efficiency may be measured and used to identify interactions between a first nucleic acid and a FRET compound as used herein. There are several ways of measuring the FRET efficiency by monitoring changes in the fluorescence emitted by the FRET donor or the FRET acceptor, which are well known by the skilled person.

In particular, Förster resonance energy transfer (FRET), fluorescence resonance energy transfer (FRET), resonance energy transfer (RET) or electronic energy transfer (EET), is a mechanism describing energy transfer between two chromophores. A donor chromophore, also referred to herein simply as donor or chromophore, initially in its electronic excited state, may transfer energy to an acceptor chromophore, also referred to herein as acceptor or quencher, through non-radiative dipole-dipole coupling. Measurements of FRET efficiency can be used to determine if (donor) chromophore and quencher are within a certain distance from each other. When both the donor and acceptor chromophore are fluorescent, the term "fluorescence resonance energy transfer" is often used.

A FRET compound as used herein may refer to a compound capable of forming a complex with a first nucleic acid wherein the FRET compound comprises a donor chromophore (e.g. a fluorescent label) which may be excited by a light source. Further, in this embodiment a first nucleic acid may be provided with an acceptor chromophore or quencher. In another embodiment, the FRET compound comprises an acceptor chromophore or quencher and the first nucleic acid comprises a donor chromophore. In another embodiment, the FRET compound may comprise both a donor chromophore and an acceptor chromophore or, in other words, a chromophore and a quencher.

A first detectable label as used herein may refer to the donor chromophore or chromophore of a FRET compound. Typically, the first detectable label or donor chromophore of the FRET compound is a fluorescent label or fluorophore.

A complexed state of a FRET compound refers to a state where the FRET compound is in complex with a first nucleic acid. An uncomplexed state of a FRET compound refers to a state where the FRET compound is not in complex with a first nucleic acid.

A first detectable characteristic of a FRET compound as used herein may refer to a state wherein emission of the chromophore, e.g. a fluorophore, is quenched. In this embodiment, a second detectable characteristic may refer to a state where emission of the chromophore, e.g. the fluorophore, is present. Accordingly, the value indicative for the presence and/or amount of first nucleic acid captured by FRET compounds in solution may be determined in a complexed state of the FRET compounds.

In other embodiments, a first detectable characteristic as used herein may refer to a state where emission of a chromophore, e.g. a fluorophore, is present. In this embodiment, a second detectable characteristic may refer to a state where emission of the chromophore, e.g. the fluorophore, is quenched.

In some embodiments, emission of the chromophore, e.g. a fluorophore, may be quenched because the donor chromophore and acceptor chromophore are in proximity, such as within a distance of 1 to 10 nm, which allows FRET between the donor chromophore and acceptor chromophore, when the FRET compound is in an uncomplexed state, i.e. not in complex with the first nucleic acid. Emission of the chromophore, e.g. the fluorophore, may be present because the donor chromophore and acceptor chromophore are not within a distance which would allow FRET between the donor chromophore and acceptor chromophore when the FRET compound is in a complexed state, i.e. in complex with the first nucleic acid.

In other embodiments, emission of the chromophore, e.g. a fluorophore, may be quenched because the donor chromophore and acceptor chromophore are in proximity, such as within a distance of 1 to 10 nm, which allows FRET between the donor chromophore and acceptor chromophore, when the FRET compound is in a complexed state, i.e. in complex with the first nucleic acid. Emission of the chromophore, e.g. the fluorophore, may be present because the donor chromophore and acceptor chromophore are not within a distance which allows FRET between the donor chromophore and acceptor chromophore when the FRET compound is in a uncomplexed state, i.e. not in complex with the first nucleic acid.

In some embodiments, the FRET compound comprises a LightCycler probe system. In this embodiment, the LightCycler probe system comprises a FRET donor compound and a FRET acceptor compound. Typically, both the FRET donor compound and the FRET acceptor compound are oligonucleotides. The FRET donor compound and the FRET acceptor compound may bind to the first nucleic acid at locations which are in proximity sufficient for FRET.

In a specific embodiment, a LightCycler probe system consists of a pair of single-stranded fluorescent labeled oligonucleotide probes. One oligonucleotide probe may be labeled at the 3'end with a donor fluorophore dye and the other oligonucleotide probe may be labeled at its 5' end with an acceptor fluorophore dyes. The free 3' hydroxyl group of the second probe may be blocked with a phosphate group to prevent DNA polymerase extension. Typically, there is a spacer of 1 to 5 nucleotides to separate the two probes from each other. During the annealing step of a PCR, PCR primers and LightCycler probes may hybridize to their specific target regions, bringing the donor dye into close proximity to the acceptor dye. When the donor dye is excited by light from a LightCycler instrument, energy is transferred by fluorescence resonance energy transfer from the donor to the acceptor dye. No energy transfer should occur when the two probes are free-floating, separated from each other in the solution. Hybridization of the probes is measured by a decrease in the donor fluorescence signal or the increase of in acceptor fluorescence signal.

In another embodiment, the FRET compound may be a molecular beacon. Molecular beacons may include oligonucleotide hybridization probes that can report the presence of a first nucleic acid in a solution. Molecular beacons are also often referred to as molecular beacon probes. Typically, molecular beacons are hairpin-shaped molecules with an internally quenched chromophore, e.g. a fluorophore whose emission, e.g. fluorescence is restored when they bind to a target nucleic acid sequence. A typical molecular beacon may be between 20 to 30 nucleotides long, such as 20, 21, 22, 23, 24, 25, 26, 27, 28, 20 or 30 nucleotides, e.g. 25 nucleotides.

The middle nucleotides such as the middle 15 nucleotides are typically complementary to the target nucleic acid and do not base pair with one another, while the nucleotide at each terminus, e.g. the 5 nucleotides at each terminus, are complementary to each other rather than to the target nucleic acid.

In particular, a typical molecular beacon structure can be divided into four parts comprising a loop which is typically an 18-30 base pair region of the molecular beacon that is complementary to the target sequence, a stem (or beacon stem) which is formed by the attachment, to both termini of the loop, of two short, e.g. 5-7 nucleotide residues, oligonucleotides that are complementary to each other, wherein at the 5' end of the molecular beacon a fluorescent dye is covalently attached, and a 3' quencher which is non-fluorescent and may be covalently attached to the 3' end of the molecular beacon. Alternatively, at the 3' end of the molecular beacon a fluorescent dye is covalently attached, and a 5' quencher which is non-fluorescent may be covalently attached to the 5' end of the molecular beacon. The preparation of molecular beacons is well documented for the skilled person.

When the molecular beacon as described above is in closed loop shape, the quencher resides in proximity to the fluorophore, which results in quenching the fluorescent emission of the latter. In this embodiment, if the first nucleic acid to be detected is complementary to the strand in the loop, the event of hybridization occurs. The duplex formed between the first nucleic acid and the loop maybe more stable than that of the stem, because the former duplex involves more base pairs. The molecular beacon probe undergoes a conformational change that forces the stem hybrid to dissociate and the fluorophore and the quencher are separated from each other restoring fluorescence. Thus, once the fluorophore is in distance from the quencher, illumination of the hybrid with light results in the fluorescent emission. The presence of the emission reports that the event of hybridization has occurred and hence the first nucleic acid sequence is present in the test sample.

In other embodiments, an FRET compound may be selected from loop tag probes, strand displacement probes or TaqMan probes.

These and other FRET compounds are well known to the skilled person. The use of FRET is described, e.g., in Marras, S. A. E. (2006) *Methods Mol Biol.* 335, 3-16; Liu, B. et al. (2005) *Proc. Natl. Acad. Sci. USA* 102, 589-593; and Szollosi, J. et al. (2002) *J. Biotechnol.* 82, 251-266 whose relevant contents are herewith explicitly referred to. For example, Marras, S. A. E. (2006) *Methods Mol Biol.* 335, 3-16 describe in detail guidelines that can be followed in choosing the appropriate fluorophore quencher combinations for different types of fluorescent hybridization probes and spectrofluorometric thermal cyclers and also describe exemplary fluorophore labels and quencher labels for fluorescent hybridization probes.

The amount of FRET compound is typically present in excess compared to a species of reporter compound, e.g. in 5- to 100-fold excess or 10- to 80-fold excess or 20- to 50-fold excess or 30- to 40-fold excess.

Further, the first nucleic acid may be present in the sample in a low copy number. In some embodiments, the first nucleic acid may be present in an amount of less than 100 copies per sample. For example, the first nucleic acid compound may be present in an amount of 80 copies or less per sample, or 70 copies or less per sample, or 60 copies or less per sample, or 50 copies or less per sample, or 40 copies or less per sample, or 20 copies or less per sample, or 10 copies or less per sample.

In another embodiment, the second nucleic acid may be present in an amount of 100 copies or more per sample, e.g. in an amount of 200 copies or more per sample, or at least 300 copies per sample, or at least 400 copies per sample, or at least 500 copies per sample, or at least 600 copies per sample, or at least 700 copies per sample, or at least 800 copies per sample, or at least 900 copies per sample, or at least 1000, at least 2000, at least 5000 or at least 10000 copies per sample.

The term "determining a value indicative for the presence and/or amount of reporter compound captured on the binding member", as used herein, may refer to the detection/determination of parameters such as electrical conductivity, redox potential, optical absorption, fluorescence intensity or bioluminescence that allow for qualitative and/or quantitative measurements of the reporter compounds captured (or re-captured) on the binding member. Only one of these parameters may be determined but it is also possible to determine more than one parameter (e.g., electrical conductivity and the intensity of a fluorescence signal caused by a suitable label), either concomitantly or consecutively.

For performing the detection reaction, the reporter compounds may be labeled with one or more detectable labels, also referred to herein as the "second detectable label". The term "second detectable label", as used herein, refers to any compound or moiety that comprises one or more appropriate chemical substances or enzymes, which directly or indirectly generate a detectable compound or signal in a chemical, physical or enzymatic reaction. Such a label may thus be necessary for or will facilitate detection of the reporter compound of interest by being capable of forming interactions with said reporter compound. As used herein, the term is to be understood to include both detectable labels as such (also referred to as "markers") as well as any compounds coupled to one or more such detectable markers. Furthermore, moieties interfering with the generation of a detectable signal by a label (e.g., a quencher "hijacking" the emissions that resulted from excitation of the fluorophore, as long the quencher and the fluorophore are in close proximity to each other) may also belong to the detectable labels. The detectable labels may be incorporated or attached to the target nucleic acids, e.g., in form of modified and/or labelled ribonucleotides, deoxynucleotides or dideoxynucleotides.

Detectable markers or labels that may be used include any compound, which directly or indirectly generates a detectable compound or signal in a chemical, physical or enzymatic reaction. Labeling can be achieved by methods well known in the art (see, for example, Sambrook, J. et al., supra; and Lottspeich, F., and Zorbas H., supra).

The labels can be selected inter alia from fluorescent labels, enzyme labels, colored labels, chromogenic labels, luminescent labels, radioactive labels, haptens, biotin, metal complexes, metals, and colloidal gold. All these types of labels are well established in the art. An example of a physical reaction that is mediated by such labels is the emission of fluorescence or phosphorescence upon irradiation or excitation or the emission of X-rays when using a radioactive label. Alkaline phosphatase, horseradish peroxidase, β-galactosidase, and β-lactamase are examples of enzyme labels, which catalyze the formation of chromogenic reaction products.

In specific embodiments, the second detectable label is a fluorescent label. Numerous fluorescent labels are well established in the art and commercially available from different suppliers (see, for example, *The Handbook—A Guide to Fluorescent Probes and Labeling Technologies*, 10th ed. (2006), Molecular Probes, Invitrogen Corporation, Carlsbad, Calif., USA).

In some embodiments, both the first detectable label of the FRET compound and the second detectable label of the reporter compound are fluorescent labels. In these embodiments, both the first detectable label and the second detectable label may emit in a wavelength range of from 300 nm to 850 nm, e.g. 450 nm to 750 nm or 550 to 650 nm. In a specific embodiment, the first detectable label and the second detectable label emit in the same wavelength, e.g. are identical, e.g. are the same fluorophore such as Cy5®. In this specific embodiment wherein the first detectable label and the second detectable label emit in the same wavelength, e.g. are identical, the amount of FRET compound is typically present in excess compared to a species of reporter compound, e.g. in 5- to 100-fold excess or 10- to 80-fold excess or 20- to 50-fold excess or 30- to 40-fold excess.

For detecting such labels, a detection system may be used which is suitable for both determining values indicative for the presence and/or amount of first nucleic acids captured by FRET compounds and for the presence and/or amount of reporter compound captured on the binding member, e.g. on a microarray. The detection system may be adapted for holding a test device as described below. Typically, the detection system is positioned opposite to the binding member. The selection of a suitable detection system depends on several parameters such as the type of labels used for detection or the kind of analysis performed. Various optical detection systems are well established in the art. A general description of detection systems that can be used with the method can be found, e.g., in Lottspeich, F., and Zorbas H., supra.

Typically, detection systems are based on the comparison of the fluorescence intensities of spectrally excited nucleic acids labeled with fluorophores. Fluorescence is the capacity of particular molecules to emit their own light when excited by light of a particular wavelength resulting in a characteristic absorption and emission behavior. In particular, quantitative detection of fluorescence signals is performed by means of modified methods of fluorescence microscopy (for review see, e.g., Lichtman, J. W., and Conchello, J. A. (2005) *Nature Methods* 2, 910-919; Zimmermann, T. (2005) *Adv. Biochem. Eng. Biotechnol.* 95, 245-265). Thereby, the signals resulting from light absorption and light emission, respectively, may be separated by one or more filters and/or dichroites and imaged on suitable detectors. Data analysis is performed by means of digital image processing. Image processing may be achieved with several software packages well known in the art (such as Mathematical Digital Image Processing, EIKONA, or Image-PRO). Suitable software for such purposes is the Iconoclust software (Clondiag Chip Technologies GmbH, Jena, Germany).

Suitable detection systems may be based on "classical" methods for measuring a fluorescent signal such as epifluorescence or darkfield fluorescence microscopy (reviewed, e.g., in: Lakowicz, J. R. (1999) *Principles of Fluorescence Spectroscopy*, 2$^{nd}$ ed., Plenum Publishing Corp., NY).

Another optical detection system that may be used is confocal fluorescence microscopy, wherein the object is illuminated in the focal plane of the lens via a point light source. The point light source, object and point light detector may be located on optically conjugated planes. Examples of such confocal systems are described in detail, for example, in Diaspro, A. (2002) *Confocal and 2-photon-microscopy: Foundations, Applications and Advances*, Wiley-Liss, Hobroken, N.J. The fluorescence-optical system is usually a fluorescence microscope without an autofocus, for example a fluorescence microscope having a fixed focus.

Further fluorescence detection methods that may also be used include inter alia total internal fluorescence microscopy (see, e.g., Axelrod, D. (1999) *Surface fluorescence microscopy with evanescent illumination*, in: Lacey, A. (ed.) *Light Microscopy in Biology*, Oxford University Press, New York, 399-423), fluorescence lifetime imaging microscopy (see, for example, Dowling, K. et al. (1999) *J. Mod. Optics* 46, 199-209), fluorescence resonance energy transfer (FRET; see, for example, Periasamy, A. (2001) *J. Biomed. Optics* 6, 287-291), bioluminescence resonance energy transfer (BRET; see, e.g., Wilson, T., and Hastings, J. W. (1998) *Annu. Rev. Cell Dev. Biol.* 14, 197-230), and fluorescence correlation spectroscopy (see, e.g., Hess, S. T. et al. (2002) *Biochemistry* 41, 697-705).

In some embodiments, the method further comprises determining a value indicative for the presence and/or amount of the second nucleic acid based on the value indicative for the presence and/or amount of reporter compound captured on the binding member. In particular, the presence and/or amount of the one or more second nucleic acids present in a particular sample may be calculated based on the difference between the presence and/or amount of reporter compound being present prior to the forming of second nucleic acid/reporter molecule complexes and the amount of reporter compound being captured on the binding member after said complex formation.

For performing the detection reaction, the reporter compound may comprise one or more detectable labels as described above. For instance, the reporter compound may comprise two detectable labels. In specific embodiments, the detectable labels are fluorescent labels as described above. The detectable labels may be incorporated or attached to the reporter molecules, e.g., in form of modified and/or labeled ribonucleotides, deoxynucleotides or dideoxynucleotides.

For detecting such labels, a test device used for performing the method may further comprise a detection system suitable for determining values indicative for the presence and/or amount of reporter compound captured on the binding member. For example, a detection system suitable for determining values indicative for the presence and/or amount of target nucleic acids captured on a binding member as described above may be used.

The detection/determination of a value indicative for the presence and/or amount of the first and/or second nucleic acids may be performed only once or more than once during the assay performed. If more than one detection step during a single assay is performed, the mean value of the results obtained may be calculated in some embodiments. The data obtained in one or more cycles of detection may be analyzed and mathematically processed using appropriate computer software known by persons skilled in the art in order to determine inter alia the presence, the length or the sequence of one or more first or second nucleic acids and/or to calculate its/their amount.

In some embodiments, determining the value indicative for the presence and/or amount of reporter compound captured on the binding member comprises time-dependent monitoring of the indicative value, e.g. the repeated performing of the determination/detection step and monitoring the course of the indicative value over time. Additionally or alternatively, determining the value indicative for the presence and/or amount of FRET compound comprises time-dependent monitoring of the indicative value, e.g. the repeated performing of the determination/detection step and monitoring the course of the indicative value over time.

In embodiments, wherein the first and/or second nucleic acids are subjected to isothermal amplification, time-dependent monitoring of the value indicative for the presence and/or amount of reporter compound captured on the binding member and/or of the value indicative for the presence and/or amount of FRET compound may comprise performing the determination/detection step every second, every 2 s, every 3, every 5, every 10, every 20, every 30, every 60, every 90, or every 120 s.

In embodiments, wherein the first and/or second nucleic acids are subjected to cyclic amplification, time-dependent monitoring of the value indicative for the presence and/or amount of reporter compound captured on the binding member and/or of the value indicative for the presence and/or amount of FRET compound may comprise performing the determination/detection step every cycle, every second cycle, every third cycle, every fourth cycle, or every fifth cycle.

In further embodiments, the value indicative for the presence and/or amount of second nucleic acid is determined based on a calibration curve correlating the value indicative for the presence and/or amount of reporter compound with the value indicative for the presence and/or amount of second nucleic acid.

In some embodiments, the method further comprises releasing the remaining subset of the amount of reporter compound from the binding member after the steps of forming complexes of a subset of the amount of reporter compound with at least a subset of the amount of second nucleic acid, capturing a remaining subset of the amount of reporter compound not in complex with a second nucleic acid on the binding member, and determining the value indicative for the presence and/or amount of reporter compound captured on the binding member. The term "releasing", as used herein, denotes the detachment or unbinding of the reporter molecules from the binding member. This may be accomplished, for example, enzymatically via the cleavage of any covalent bonds or in cases, where the nucleic acid reporter molecules are bound to the binding member by reporter specific nucleic acid capture molecules via complementary base-pairing, by increasing the temperature in the reaction chamber, in which the assay is performed, thus resulting in nucleic acid strand separation (i.e. denaturation).

In further embodiments, the steps of releasing, forming complexes, capturing, and determining are repeated N additional times, where N is an integer greater than or equal to 1. In other words, the method is performed in a cyclic manner. In specific embodiments, the integer N is ≥5, ≥10 or ≥20.

Further, the step of forming complexes of a subset of the amount of reporter compound with at least a subset of the amount of second nucleic acid and the step of capturing a remaining subset of the amount of reporter compound not in complex with a second nucleic acid on the binding member may be performed concomitantly.

In other embodiments, the steps of (i) forming complexes each comprising a first nucleic acid and a FRET compound, (ii) forming complexes of a subset of the amount of reporter compound with at least a subset of the amount of second nucleic acid and (iii) capturing a remaining subset of the amount of reporter compound not in complex with a second nucleic acid on the binding member may be performed concomitantly.

In some embodiments, the method further comprises subjecting the first and second nucleic acids to amplification, that is, to increase their amount present in the sample before subjecting the same to the further analysis in order to facilitate further detection.

Amplification of the first and second nucleic acid may be initiated prior to the step of forming complexes of a subset of the amount of reporter compound with at least a subset of the amount of second nucleic acid. In particular, the multiple nucleic acids may be subjected to amplification while allowing reporter compounds to form a complex with a second nucleic acid, and reporter compounds not in complex with a second nucleic acid to be re-captured on the binding member.

In a specific embodiment, the steps of (i) forming complexes each comprising a first nucleic acid and a FRET compound, (ii) forming complexes of a subset of the amount of reporter compound with at least a subset of the amount of second nucleic acid, (iii) capturing a remaining subset of the amount of reporter compound not in complex with a second nucleic acid on the binding member, and (iv) subjecting the first and/or second nucleic acid to amplification are performed concomitantly.

Typically, nucleic acid amplification is achieved by means of an isothermal amplification method. Amplifying nucleic acids in isothermal conditions makes it possible to avoid the use of a thermocycling apparatus. There are several types of isothermal nucleic acid amplification methods known to the skilled person, including transcription-mediated amplification, nucleic acid sequence-based amplification, signal-mediated amplification of RNA technology, strand displacement amplification, rolling circle amplification, loop-mediated isothermal amplification, isothermal multiple displacement amplification, helicase-dependent amplification, single primer isothermal amplification, and circular helicase-dependent amplification. Isothermal nucleic acid amplification technologies are reviewed for example in P. Gill and A. Ghaemi, Nucleosides Nucleotides Nucleic Acids, 27(3): 224-243 (2008).

An exemplary isothermal amplification for use in the methods described herein is nicking enzyme amplification reaction (NEAR) which may employ a strand-displacing DNA polymerase initiating at a nick created by a nicking enzyme, rapidly producing many short nucleic acids from the target sequence.

Another exemplary isothermal amplification for use in the methods described herein is loop-mediated isothermal amplification (LAMP) which uses e.g. 4 to 6 primers recognizing e.g. 6 to 8 distinct regions of target DNA. A strand-displacing DNA polymerase initiates synthesis and two of the primers may form loop structures to facilitate subsequent rounds of amplification.

Another exemplary isothermal amplification for use in the methods described herein is strand displacement amplification (SDA) which relies on a strand-displacing DNA polymerase, typically Bst DNA Polymerase, Large Fragment or Klenow Fragment (3'-5' exo-), to initiate at nicks created by a strand-limited restriction endonuclease or nicking enzyme at a site contained in a primer. The nicking site is regenerated with each polymerase displacement step, resulting in exponential amplification.

Another exemplary isothermal amplification for use in the methods described herein is helicase-dependent amplification (HDA) which employs the double-stranded DNA unwinding activity of a helicase to separate strands, enabling primer annealing and extension by a strand-displacing DNA polymerase. Like PCR, this system requires only two primers.

In some embodiments, FRET compounds as described above such as molecular beacons are used for determining the presence and/or amount of first nucleic acid and reporter compounds as described above are used for determining the presence and/or amount of second nucleic acid during the isothermal amplification. In such embodiments, the presence and/or amount of first nucleic acid may be determined by means of a FRET compound such as a molecular beacon which specifically binds to the first nucleic acid and which generates a signal in solution as described above depending on the amount of amplified first nucleic acid present in solution. The presence and/or amount of second nucleic acid may be determined by detecting a signal generated on the surface of the binding member such as a microarray by a labeled reporter compound which specifically binds both to the second nucleic acid and to a reporter specific capture molecule attached to the surface of the binding member, e.g. a microarray.

In alternative embodiments, nucleic acid amplification is achieved by means of a cyclic amplification. The cyclic amplification may comprise any number of amplification cycles that is equal or greater than two. Usually, cyclic amplification reaction comprises at least 10 or at least 20 cycles. An exemplary cyclic amplification is a polymerase chain reaction (PCR). PCR is an established standard method in molecular biology that is described in detail, e.g., in Sambrook et al., supra; and in Ausubel, F. M. et al., supra. Typically, PCR is used for the amplification of double-stranded DNA molecules by employing a thermostable DNA polymerase.

In some embodiments, the DNA polymerase used in the amplification has exonuclease activity, particularly 5'→3' exonuclease activity. Examples of such DNA polymerases include inter alia Taq DNA polymerase or Tth DNA polymerase (which are commercially available from multiple providers). By means of this 5'→3' exonuclease activity the DNA polymerase may nucleolytically attack the labeled 5'-termini of reporter molecules that are bound to the second nucleic acids resulting in a progressive degradation of such reporter molecules. As a result, the amount of reporter compound that is captured on the binding member additionally decreases during the amplification reaction. Optionally, the DNA polymerase employed may also exhibit 3'→5' exonuclease activity ("proofreading activity") for removing an incorrect nucleotide that has been added to the nascent DNA strand at a particular sequence position. Examples of such DNA polymerases having both exonuclease activities include inter alia Pwo DNA polymerase, and Pfu DNA polymerase (both enzymes are also commercially available from various suppliers). DNA polymerases having a 5'→3' exonuclease activity are typically used if a degradation of a reporter compound is desirable in order to generate and/or enhance a detectable signal.

In some embodiments, FRET compounds as described above such as TaqMan probes are used for determining the presence and/or amount of first nucleic acid and reporter compounds as described above are used for determining the presence and/or amount of second nucleic acid during the cyclic amplification. In such embodiments, the presence and/or amount of first nucleic acid may be determined by means of a FRET compound such as a TaqMan probe which specifically binds to the first nucleic acid and which generates a signal in solution as described above depending on the amount of amplified first nucleic acid present in solution. The presence and/or amount of second nucleic acid may be determined by detecting a signal generated on the surface of the binding member such as a microarray by a labeled reporter compound which specifically binds both to the second nucleic acid and to a reporter specific capture molecule attached to the surface of the binding member, e.g. a microarray.

If the first and/or second nucleic acid is a RNA molecule, the method may further comprise subjecting the first and/or second nucleic acid to reverse transcription as described above prior to subjecting them to amplification. Reverse transcription is another standard method in molecular biology and also described, e.g., in Sambrook et al., supra; and in Ausubel, F. M. et al., supra.

In typical embodiments of a method of determining the presence and/or amount of a nucleic acid, e.g. a first nucleic acid in a sample, amplification controls may be used to detect inhibitors of amplification. In particular, the second nucleic acid may be an internal control nucleic acid selected from the group consisting of an internal positive amplification control and an internal negative amplification control. Such control nucleic acids may be added to the sample, e.g. a body fluid sample as described above.

Construction of internal amplification controls can be performed in several ways, at the choice and discretion of the skilled person. The source of internal amplification controls may be plasmid DNA carrying the cloned internal amplification control sequence or purified PCR products. In some embodiments, the internal control nucleic acid is an artificial nucleic acid which, under usual conditions, is naturally not present in a body fluid sample to be analysed. For example, the internal control nucleic acid is armored RNA which can be reverse transcribed before amplification.

An internal positive amplification control nucleic acid or competitive internal amplification control nucleic acid or internal positive control may be designed from partial or full sequences of target analyte. In particular, the first nucleic acid and the internal positive amplification control nucleic acid may have identical primer-binding sites. For example, the internal positive amplification control nucleic acid may have a sequence corresponding to a partial sequence of the first nucleic acid. Sharing the same primer-binding site may allow for similar or essentially the same amplification conditions. To avoid competition between the first nucleic acid and the internal positive amplification control nucleic acid, corresponding amplicon primers may be provided in excess.

Further, in this embodiment, reporter compound binding sites on the binding member, e.g. reporter specific capture probes, may be specific for the internal positive amplification control nucleic acid to allow discrimination between the internal positive amplification control nucleic acid and optionally other control nucleic acids on the binding member.

An internal negative amplification control nucleic acid or non-competitive internal amplification control nucleic acid may be a nucleic acid essentially without sequence homology to a target analyte or an internal positive amplification control nucleic acid. For example, the internal negative amplification control nucleic acid may have a sequence which does not comprise a primer binding site for amplicon primers which are used to amplify the target analyte or first nucleic acid or internal positive amplification control nucleic acid.

Further, in this embodiment, reporter compound binding sites on the binding member may be specific for the internal negative amplification control nucleic acid to allow discrimination between the negative amplification control nucleic acid, the internal positive amplification control nucleic acid and other control nucleic acids on the binding member. In the absence of amplification of the internal negative amplification control nucleic acid the signal on reporter compound binding sites specific for reporter compounds capable for forming complexes with the internal negative amplification control nucleic acid is expected to remain essentially constant during the process. For example, for a valid test, the signal on reporter compound binding sites specific for reporter compounds capable for forming complexes with the internal negative amplification control nucleic acid may need to remain constant with no reported Ct value, otherwise the test may be considered as not valid.

Other controls may also be used in the methods described herein. For example in addition or alternatively to the internal amplification control described herein, controls may be selected from a positive hybridization control, a processing-positive control, a processing-negative control, and a reagent control.

A positive hybridization control may be a reporter compound which is not capable of forming complexes with any of the first and second nucleic acid.

A processing positive control may be a negative sample spiked with a sufficient amount of target analyte and processed throughout the entire protocol.

A processing negative control may refer to a negative sample spiked with a sufficient amount of closely related, but non-target analyte processed throughout the entire protocol.

A non-template control (blank) may refer to a control containing all reagents, but no target or internal amplification control nucleic acids.

For nucleic acid amplification, a test device may be used for performing the method which may comprise one or more temperature control units and/or temperature regulating units for controlling and/or regulating the temperature within the structure or reaction chamber. Such a temperature control unit and/or temperature regulating unit may comprise one or more separate heating and/or cooling elements, which may directly contact a reaction chamber of the test device. Typically, the one or more heating and/or cooling elements are made of a heat conductive material. Examples of such heat conductive materials include inter alia silicon, ceramic materials like aluminium oxide ceramics, and/or metals like high-grade steel, aluminium, copper, or brass. An exemplary detailed description of a temperature control unit and/or temperature regulating suitable for performing the methods described herein can also be found in WO 01/02094, whose relevant contents are herewith explicitly referred to.

Measuring the temperature in the reaction chamber can be performed by various methods well established in the art, e.g. by using integrated resistance sensors, semi-conductor sensors, light waveguide sensors, polychromatic dyes or liquid crystals. Furthermore, the temperature in the reaction chamber can be determined by using an integrated temperature sensor in the chamber body, a pyrometer or an infrared sensor, or by measuring the temperature-dependent alteration of parameters such as the refraction index at the surface on which detection takes place or the pH value of the sample, for example by measuring the colour alteration of a pH-sensitive indicator.

In some embodiments, e.g. for safety reasons, the reaction chamber may be irreversibly sealed prior to initiating amplification of the nucleic acids. Irreversibly sealing the reaction chamber may be achieved by sealing an inlet and, optionally, an outlet of the reaction chamber. For instance, a channel and/or a value connected with the reaction chamber may be heat-sealed or welded. Plastics channels or valves may be heat-sealed by contacting a hot pin with the channel or valve so that the plastics are melted and the channel or valve is locked.

The step of providing the first and/or second nucleic acids may comprise releasing the first and/or second nucleic acids from biological material comprised in the sample. To this end, the sample may be heated in order to destroy cellular membranes and/or viral capsids (e.g., by employing a temperature control unit and/or temperature regulating unit as described above). In some embodiments, this releasing step comprises contacting the fluid sample with a lysing reagent, for example a reagent comprising one or more detergents which disintegrate the cellular membranes and/or viral capsids. Such lysing reagents are well known in the art (see, for example, Sambrook, J. et al. (1989) *Molecular, Cloning: A Laboratory Manual,* 2nd ed., Cold Spring Harbor Laboratory Press, Cold Spring Harbor, N.Y.) and commercially available by many suppliers.

The method may further comprise separating the first and/or second nucleic acids from concomitant material.

The value indicative for the presence and/or amount of first nucleic acid captured by FRET compounds and the value indicative for the presence and/or amount of reporter compound captured on the binding member may be determined consecutively or concomitantly.

Next, embodiments of a test device or assay system or micro fluidic cartridge will be discussed, typically capable of performing most and for example all steps of the methods described herein. Exemplary test devices, reaction chambers and corresponding methods are also described in WO 2005/108604, WO 2008/055915, WO 2008/135564 and T. Ulrich et al., PloS ONE, 7, 4, e35438 (2012), whose relevant contents are herewith explicitly referred to. In particular, the methods described herein may be performed in a test device enabling determination of values indicative for the presence and/or amount of reporter compounds captured on the binding member during amplification by removing background signals from the solution. In one embodiment, this removal of solution from the reaction chamber of a test device is reversible. For example, for the amplification and detection, a test device comprising a reaction chamber as described below may be used.

In particular, the value indicative for the presence and/or amount of first nucleic acid captured by FRET compounds in solution and/or the value indicative for the presence and/or amount of reporter compound captured on the binding member may be determined in a reaction chamber comprising the binding member and a cover element. The binding member may be arranged on the cover element or on a surface opposite to the cover element. In these embodiments, the cover element may be configured to be at least partially deformable such that the reaction chamber has a relaxed state interior volume and a compressed state interior volume.

In a specific embodiment, the value indicative for the presence and/or amount of first nucleic acid captured by FRET compounds in solution and/or the value indicative for the presence and/or amount of reporter compound captured on the binding member may be determined in a reaction chamber comprising a first surface, a second surface and the binding member capable of capturing the reporter compound, wherein the distance between the first and the second surface can be varied such that the reaction chamber has a relaxed state interior volume and a compressed state interior volume.

In particular, in a reaction chamber having a compressed state interior volume liquid comprising detectable label which has not bound to the binding member is removed from the area between the binding member and a surface of the reaction chamber opposite to the binding member. Accordingly, in a reaction chamber having a relaxed state interior volume liquid comprising detectable label which has not bound to the binding member is not removed from the area between the binding member and a surface of the reaction chamber opposite to the binding member.

In particular, the value indicative for the presence and/or amount of first nucleic acid captured by FRET compounds is determined in the reaction chamber having a relaxed state interior volume. Further, the value indicative for the presence and/or amount of reporter compound captured on the binding member may be determined in the reaction chamber having a compressed state interior volume.

For example, determining a value indicative for the presence and/or amount of the captured reporter compounds may be performed with an actuator actuated to deform the flexible cover element. The cover element may be deformed in such a way that the volume of the reaction chamber is reduced. In such an embodiment, the volume of the reaction chamber may be increased again after determining a value indicative for the presence and/or amount of the captured reporter compounds. In addition or alternatively, during detection an actuator may compress the reaction chamber to reduce the distance between the flexible cover element and the substrate thereby removing liquid comprising material which has not bound to the binding member from the detection zone.

In an exemplary embodiment, the binding member is provided in the reaction chamber and the steps of forming complexes each comprising a first nucleic acid and a FRET compound; forming complexes of a subset of the amount of reporter compound with a second nucleic acid; and capturing a remaining subset of the amount of reporter compound not in complex with a second nucleic acid on the binding member are performed in the reaction chamber. Further, subjecting first and/or second nucleic acids to amplification and/or (re-)capturing the reporter compounds with respect to the binding member may also be performed in the reaction chamber.

Providing the first and/or second nucleic acids may be performed spatially separated from the steps of forming complexes each comprising a first nucleic acid and a FRET compound, forming complexes of a subset of the amount of reporter compound with a second nucleic acid; subjecting the first and/or second nucleic acids to amplification, capturing a remaining subset of the amount of reporter compound not in complex with a second nucleic acid on the binding member, determining a value indicative for the presence and/or amount of first nucleic acid captured by FRET compounds, and determining a value indicative for the presence and/or amount of reporter compound captured on the binding member.

The methods described herein may e.g. be performed in a test device comprising a reaction chamber adapted for accommodating liquids, wherein the reaction chamber comprises at least one binding member and is e.g. in fluid communication with a microfluidic network. For example, the method may be performed in a test device comprising a rigid substrate, a flexible cover element at least partially covering the substrate, a structure or reaction chamber formed in the substrate, adapted for accommodating liquids and comprising at least one binding member adapted for capturing the reporter compounds and for determining a value indicative for the presence and/or amount of reporter compound, optionally a microfluidic network interconnecting at least the reaction chamber with further structures, e.g. structures for providing the first and/or second nucleic acids. The test device may be placed with respect to or into a detector system. Such a detector system may comprise an actuator unit adapted for pressing the flexible cover element against the rigid substrate.

An exemplary test device is schematically shown in FIG. 1. The mechanical module of such a test device may contain a plunger or actuator (a) that is used to reversibly squeeze and release a reaction chamber of the test device. The temperature control module may comprise two peltier elements with an aperture in the center (b). Fluorescence images of the binding member (c), e.g. an array, may be acquired by an optical detection module (d). Synchronized simultaneous performance of all components may be controlled by the process control module (e), which also controls the thermal regime of the amplification reaction. After image acquisition, the hybridization pattern is analyzed by the image analysis module. Results may be visualized as a plot of intensity on each individual probe of the binding member versus reaction time.

Figure 2:
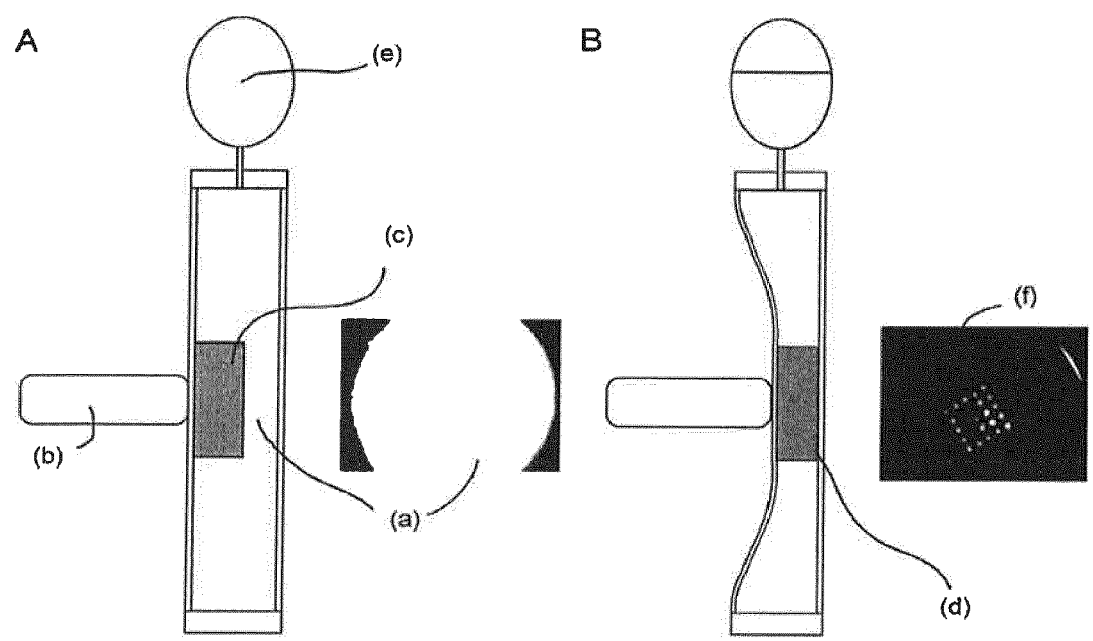
FIG. 2 is a schematic drawing of a reaction chamber as described herein.

An exemplary reaction chamber is schematically shown in FIG. 2. The uncompressed reaction chamber of the test device may be filled with a reaction mix containing a high concentration of fluorescently labeled reporter probes. Therefore, imaging of the hybridization pattern on the binding member, e.g. a capture probe array, against the background is not feasible (a). For image acquisition, pressure by means of a plunger or actuator (b) may be applied and the binding member (c) is pressed tightly against the top side of the reaction chamber, thus displacing the fluorescent liquid (d). Displaced liquid may be pressed into an integrated pneumatic spring (e). After image acquisition (f) the reaction chamber is allowed to relax and the liquid sample can return into the relaxed reaction chamber.

Figure 3:
FIG. 3 shows fluorescence images of the bulk (solution) and a microarray which were alternately made in an exemplary embodiment of the methods described herein.

In an exemplary method performed in a test device and reaction chamber as described above, the sample may contain competitive reporter compounds and molecular beacons which change the fluorescence signal in the sample as soon as an amplicon specific for the donor chromophore is formed. The binding member may comprise a microarray comprising reporter-specific capture compounds which are suitable for forming complexes with the reporter compounds and generate a fluorescence signal on the microarray. The reporter compounds are further specific for a sequence in the amplification product, e.g. a mimic fragment which is used as an internal positive amplification control or as an internal negative amplification control. After starting the reaction, images of the solution and the microarray are alternately made (see FIG. 3).

Figure 4:
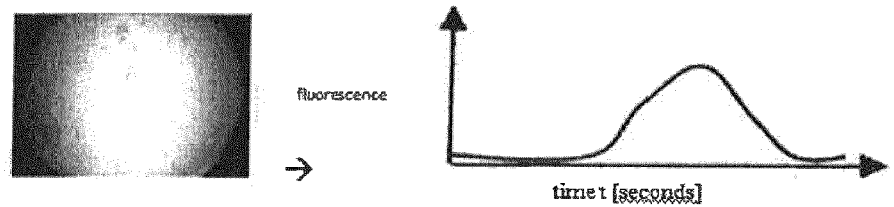
FIG. 4 shows data analysis made separately with the fluorescence images of FIG. 3 resulting from the bulk (solution, see FIG. 4a) and the images resulting from the microarray (see FIG. 4b).
Figure 4:
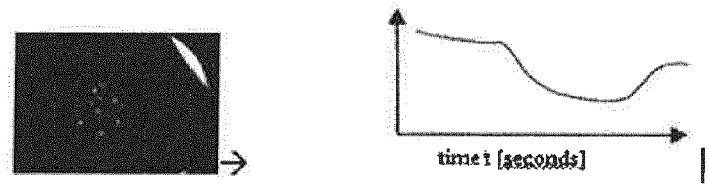

Data analysis is made separately with the images resulting from the solution and the images resulting from the microarray (see FIG. 4).

As described in FIG. 4a), the fluorescence intensity in solution increases due to the formation of complexes of the molecular beacons with the synthesized amplification product of the first nucleic acid. Shown in FIG. 4a) is a characteristic curve for a NEAR amplification. FIG. 4b) shows the decrease of the fluorescence signal due to the binding of the reporter compounds to the synthesized amplification product of the second nucleic acid in solution.

The methods described herein may be used in immunoassays and point-of-care nucleic acid tests.

The following examples are solely for the purpose of illustrating specific embodiments, and are not to be construed as limiting the scope of the disclosure in any way.

Example 1

Tuberculose DNA was amplified by using an isothermal NEAR in a test device as described in FIGS. 1 and 2 comprising a compressible reaction chamber and an array as the binding member capable of capturing reporter compounds. The sample included primers (reverse primer: Tb_DR_R25c 5'-AGACTCCATATGGAGTCT- CATCTTTCCGTCCCC-3', forward primer: Tb_DR_F16 5'-CGACTCCATATGGAGTCGTCGTCAGACCCAAAA-3'); molecular beacon MB_P2_7 (5'-TCGGGGCAGAC-CCAAAACCCCGA-3'); reporter compound Anti_Tb_Target_CMA (5'-CCCAAAACCCCGAGAGG-3'); enzymes (nicking enzyme and strand displacement enzyme) and a target DNA. As a control reaction, the amplification was conducted without target DNA, i.e. without template control. The amplification was conducted at 56° C. for 600 seconds. Images were acquired every 15 seconds. Results are shown in FIGS. 5a) and 5b).

Figure 5A:
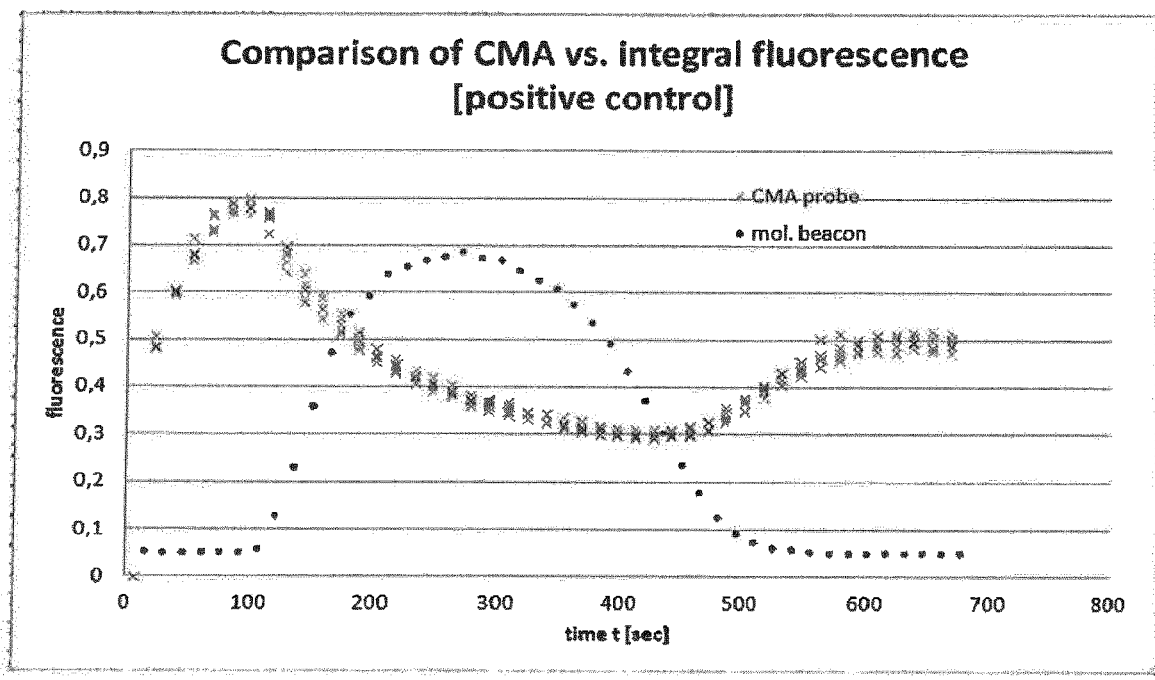
FIG. 5a) shows a comparison of competitive reporter monitored amplification and molecular beacon in the presence of target DNA.

As can be seen in FIG. 5a), which shows a comparison of competitive reporter monitored amplification and molecular beacon, the fluorescence in solution is increased due to the formation of complexes of the molecular beacon with the target DNA. Further, it can also be seen that the signal of the reporter compound on the array decreases because the reporter compound forms a complex with the NEAR amplification product.

Figure 5B:
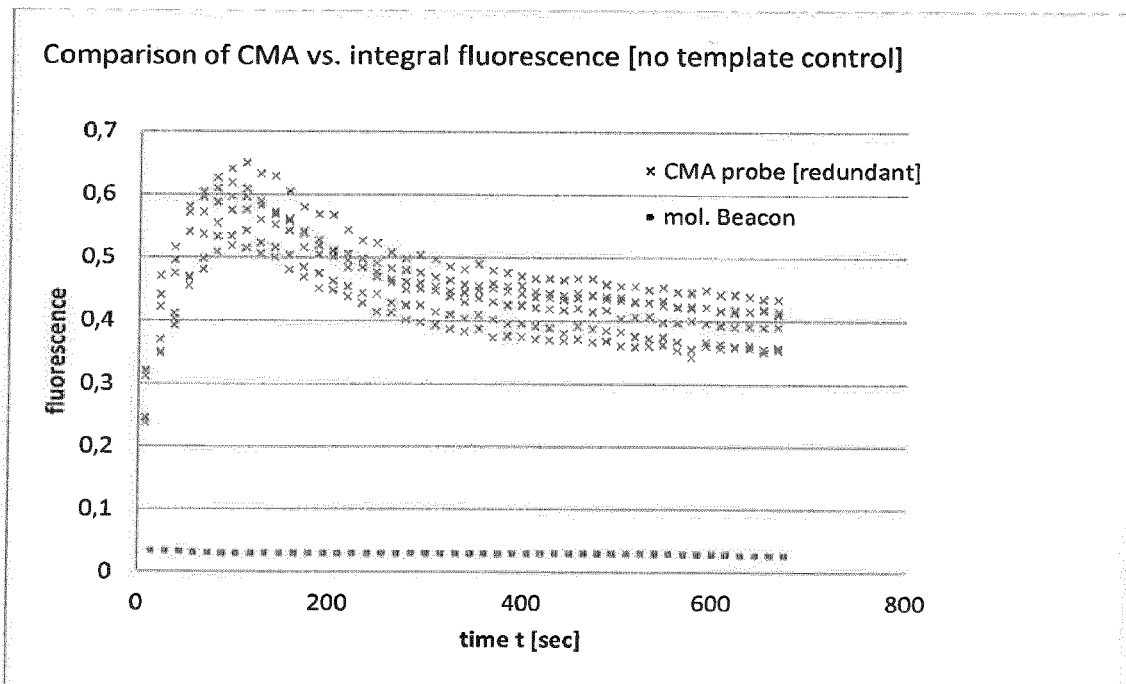
FIG. 5b) showing a comparison of competitive reporter monitored amplification and molecular beacon in the control reaction without target DNA.

As can seen from FIG. 5b) showing a comparison of competitive reporter monitored amplification and molecular beacon in the control reaction without target DNA, it can be seen that due to the absence of target DNA, fluorescence in solution remains constant over time. Further, apart from the typical bleaching effect, the reporter compound signal on the array does not decrease.

Example 2

Detection of Tuberculosis DNA in Presence of an Internal Positive Control (IPC) and a Positive Hybridization Control (PHC)

Tuberculose DNA (target DNA) and internal positive control DNA (IPC) were amplified by using an isothermal NEAR in a test device as described in FIGS. 1 and 2 comprising a compressible reaction chamber and an array as the binding member capable of capturing reporter compounds. The templates for target analyte and IPC had the same sequences in the primer binding sites, but differed in the sequences of the binding sites for the reporter compounds and the FRET compounds (here a molecular beacon), respectively. Both amplicons could therefore be amplified by the same primers and could be detected independently from each other by different probes.

The amplification reaction mix included primers (reverse primer TB_DR_25c, forward primer TbDR_F16), molecular beacon MB_PS_7, IPC reporter compound and IPC. Further, a reporter compound which is not capable of forming complexes with the IPC amplicon was added as a positive hybridization control (PHC: 5'-ccgactactacgggacgctggga-3') in order to show that the change in signal intensity of the TPC reporter is specific for the presence of the IPC amplicon. This PHC control therefore differs from the IPC reporter in its hybridization kinetics.

Figure 6:
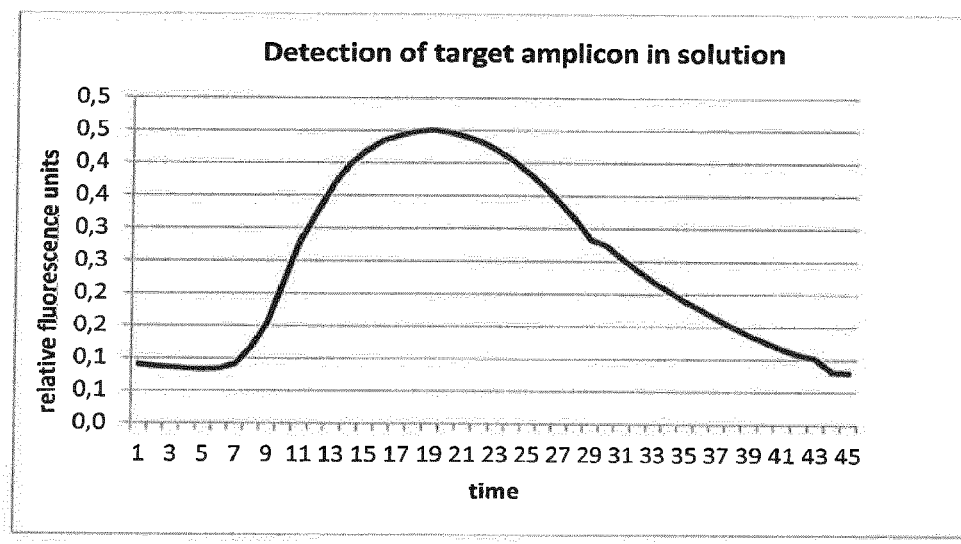
FIG. 6 shows the time course of fluorescence signal intensity in solution (detection of first/target nucleic acid).
Figure 7:
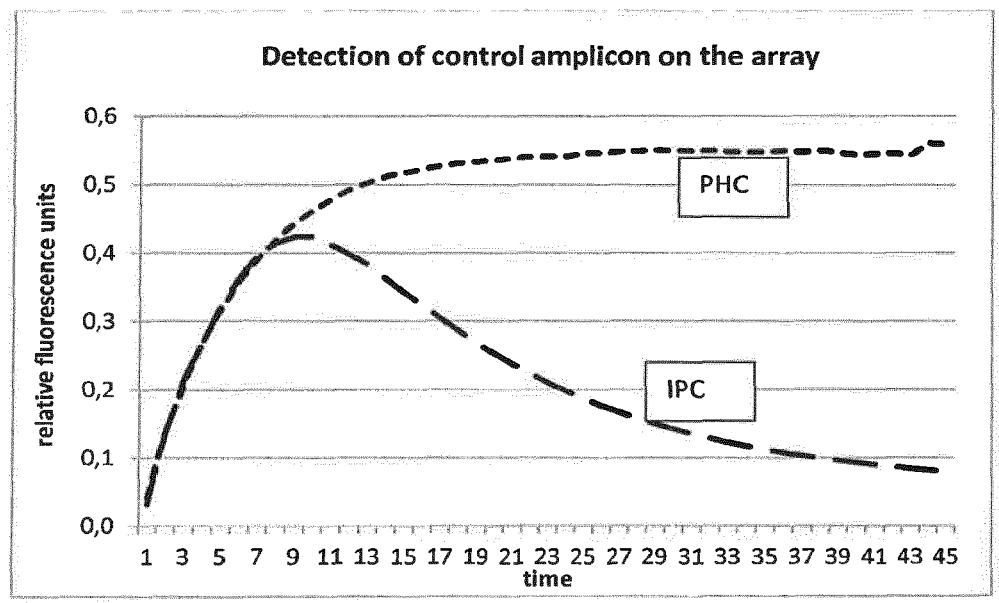
FIG. 7 shows the time course of fluorescence signal intensity on the array for IPC (internal positive control) and PHC (positive hybridsation control). Due to the absence of a competitor in solution the signal intensity course of PHC has second order kinetics.

Template Target: 100 GE (genome equivalents)
Template IPC 500 GE
Concentration forward primer 750 nM
Concentration reverse primer 50 nM
Reporter concentration IPC: 10 nM
Reporter concentration PHC: 10 nM
Concentration molecular beacon 200 nM Amplification was carried out at 56° C. for about 600 s. Images were taken every 15 seconds. The results are shown in FIGS. 6 and 7.

Although the internal positive control DNA is initially present in a 5-fold excess compared to the target DNA the target DNA can be detected in the same assay with the internal positive control DNA (detection of target analyte captured by FRET compound in solution and detection of internal positive control reporter on the array). Due to the absence of a competitor in solution the signal intensity course of PHC has second order kinetics.

Some embodiments relate to:
1. A method of determining the presence and/or amount of nucleic acids in a sample, comprising
   (a) providing
      an amount of a first nucleic acid;
      an amount of a second nucleic acid;
      an amount of a FRET compound capable of forming complexes with the first nucleic acid, wherein the FRET compound comprises a binding portion specific to a region of the first nucleic acid, and a first detectable label that has, in an uncomplexed state, a first detectable characteristic and, in a complexed state, a second detectable characteristic;
      an amount of a reporter compound capable of forming complexes with the second nucleic acid, wherein each reporter compound comprises a binding portion specific to a region of the second nucleic acid and a second detectable label; and
      a binding member capable of capturing the reporter compound;
      wherein forming of complexes of the second nucleic acid with the reporter compound inhibits capturing of the reporter compound by the binding member;
   (b) forming complexes each comprising a first nucleic acid and a FRET compound;
   (c) forming complexes of a subset of the amount of reporter compound with a second nucleic acid;
   (d) capturing a remaining subset of the amount of reporter compound not in complex with a second nucleic acid on the binding member;
   (e) determining a value indicative for the presence and/or amount of first nucleic acid captured by FRET compounds; and
   (f) determining a value indicative for the presence and/or amount of reporter compound captured on the binding member.
2. The method of embodiment 1, further comprising determining a value indicative for the presence and/or amount of second nucleic acid based on the value indicative for the presence and/or amount of reporter compound captured on the binding member.
3. The method of embodiment 1 or 2, wherein the first detectable label is a fluorescent label.
4. The method of any of embodiments 1 to 3, wherein the second detectable label is a fluorescent label.
5. The method of any of embodiments 1 to 4, wherein both the first detectable label and the second detectable label are fluorescent labels.
6. The method of embodiment 5, wherein both the first detectable label and the second detectable label emit in a wavelength range of from 300 nm to 850 nm.
7. The method of embodiment 5 or 6, wherein both the first detectable label and the second detectable label are identical.
8. The method of any of embodiments 1 to 7, wherein the value indicative for the presence and/or amount of first nucleic acid captured by FRET compounds is determined in a complexed state of the FRET compounds.
9. The method of any of embodiments 1 to 8, wherein the first nucleic acid is an analyte.

10. The method of any of embodiments 1 to 9, wherein the second nucleic acid is selected from the group consisting of a second analyte and a control nucleic acid.
11. The method of any of embodiments 1 to 10, wherein the first nucleic acid is present in an amount of less than 100 copies per sample.
12. The method of any of embodiments 1 to 11, wherein the second nucleic acid is present in an amount of 100 copies or more per sample.
13. The method of any of embodiments 1 to 12, wherein the steps of (i) forming complexes each comprising a first nucleic acid and a FRET compound, (ii) forming complexes of a subset of the amount of reporter compound with at least a subset of the amount of second nucleic acid and (iii) capturing a remaining subset of the amount of reporter compound not in complex with a second nucleic acid on the binding member are performed concomitantly.
14. The method of any of embodiments 1 to 13, further comprising subjecting the first and/or second nucleic acid to amplification, optionally wherein amplification of the first and second nucleic acid is initiated prior to the step of forming complexes of a subset of the amount of reporter compound with at least a subset of the amount of second nucleic acid.
15. The method of embodiment 14, wherein the steps of (i) forming complexes each comprising a first nucleic acid and a FRET compound, (ii) forming complexes of a subset of the amount of reporter compound with at least a subset of the amount of second nucleic acid, (iii) capturing a remaining subset of the amount of reporter compound not in complex with a second nucleic acid on the binding member, and (iv) subjecting the first and/or second nucleic acid to amplification are performed concomitantly.
16. The method of embodiment 14 or 15, wherein the second nucleic acid is selected from the group consisting of a positive amplification control and a negative amplification control.
17. The method of any of embodiments 1 to 16, wherein the binding member comprises one or more different reporter specific capture compounds being capable of capturing a reporter compound on the binding member.
18. The method of embodiment 17, wherein the reporter specific capture compounds are oligonucleotides.
19. The method of embodiments 17 and 18, wherein the different reporter specific capture compounds are arranged on different locations with respect to the binding member.
20. The method of any of embodiments 17 to 19, wherein the reporter compounds are captured on the binding member by forming complexes with the reporter specific capture compounds.
21. The method of any of embodiments 17 to 20, wherein at least a part of an interaction site of the reporter compound being capable of forming a complex with a second nucleic acid is also capable of forming a complex with a reporter specific capture compound.
22. The method of any of embodiments 17 to 21, wherein the reporter specific capture compounds and the second nucleic acid compete for forming a complex with the reporter compound.
23. The method of any of embodiments 1 to 22, wherein the value indicative for the presence and/or amount of first nucleic acid captured by FRET compounds and/or the value indicative for the presence and/or amount of reporter compound captured on the binding member is determined in a reaction chamber comprising the binding member and a cover element.
24. The method of embodiment 23, wherein the cover element is configured to be at least partially deformable such that the reaction chamber has a relaxed state interior volume and a compressed state interior volume.
25. The method of embodiment 24, wherein the value indicative for the presence and/or amount of first nucleic acid captured by FRET compounds is determined in the reaction chamber having a relaxed state interior volume.
26. The method of embodiment 23 to 25, wherein the value indicative for the presence and/or amount of reporter compound captured on the binding member is determined in the reaction chamber having a compressed state interior volume.
27. The method of any of embodiments 1 to 26, wherein the value indicative for the presence and/or amount of first nucleic acid captured by FRET compounds and the value indicative for the presence and/or amount of reporter compound captured on the binding member are determined consecutively or concomitantly.
28. The method of any of embodiments 1 to 27, wherein the reporter compounds are oligonucleotides.
29. The method of any of embodiments 1 to 28, further comprising subjecting the first and/or second nucleic acids to reverse transcription prior to subjecting them to amplification.
30. The method of any of embodiments 14 to 29, wherein the amplification comprises a step of denaturing double stranded nucleic acids, wherein the double stranded nucleic acids comprise complexes of reporter compounds with second nucleic acids, complexes of reporter compounds with reporter specific capture compounds, double strands of reporter compounds and double strands of first and/or second nucleic acids, and/or wherein the amplification comprises a step of annealing primer compounds to first and/or second nucleic acids, wherein optionally the annealing step is performed concomitantly with the step of forming complexes of a subset of the amount of reporter compound with at least a subset of the amount of second nucleic acid and/or the step of capturing a remaining subset of the amount of reporter compound not in complex with a second nucleic acid on the binding member.
31. The method of any of embodiments 14 to 30, wherein the amplification is an isothermal amplification method, wherein the isothermal amplification method optionally is an isothermal NEAR.
32. The method of any of embodiments 14 to 30, wherein the amplification is a cyclic amplification, wherein the cyclic amplification optionally is a PCR, wherein performing the PCR optionally comprises using a polymerase having exonuclease activity, wherein optionally the value indicative for the presence and/or amount of reporter compound captured on the binding member is determined after at least one cycle of the cyclic amplification, and optionally after each cycle of the cyclic amplification, wherein optionally the value indicative for the presence and/or amount of first and/or second nucleic acid is determined each time after determining the value indicative for the presence and/or amount of reporter compound captured on the binding member.
33. The method of any of embodiments 2 to 32, wherein the value indicative for the presence and/or amount of second nucleic acid is determined based on a calibration curve correlating the value indicative for the presence and/or amount of reporter compound with the value indicative for the presence and/or amount of second nucleic acid.

34. A method of determining the presence and/or amount of nucleic acids in a sample, comprising providing in a reaction chamber an amount of a first nucleic acid; an amount of a second nucleic acid; an amount of a FRET compound capable of forming complexes with the first nucleic acid, wherein the FRET compound comprises a binding portion specific to a region of the first nucleic acid, and a first detectable label that has, in an uncomplexed state, a first detectable characteristic and, in a complexed state, a second detectable characteristic; and an amount of a reporter compound capable of forming complexes with the second nucleic acid, wherein each reporter compound comprises a binding portion specific to a region of the second nucleic acid and a second detectable label; wherein the reaction chamber comprises a binding member capable of capturing the reporter compound, wherein forming of complexes of the second nucleic acid with the reporter compound inhibits capturing of the reporter compound by the binding member, and a cover element which is configured to be at least partially deformable such that the reaction chamber has a relaxed state interior volume and a compressed state interior volume; subjecting the first and/or second nucleic acid to amplification;

forming complexes each comprising a first nucleic acid and a FRET compound;

forming complexes of a subset of the amount of reporter compound with a second nucleic acid;

capturing a remaining subset of the amount of reporter compound not in complex with a second nucleic acid on the binding member;

determining a value indicative for the presence and/or amount of first nucleic acid captured by FRET compounds in solution in the reaction chamber having a relaxed state interior volume; and determining a value indicative for the presence and/or amount of reporter compound captured on the binding member in the reaction chamber having a compressed state interior volume, and, based on the value indicative for the presence and/or amount of reporter compound captured on the binding member, determining a value indicative for the presence and/or amount of second nucleic acid.

The invention claimed is:

1. A method of determining the presence and/or amount of nucleic acids in a sample, comprising
   (a) providing
      an amount of a first nucleic acid;
      an amount of a second nucleic acid;
      an amount of a FRET compound capable of forming complexes with the first nucleic acid, wherein the FRET compound comprises a binding portion specific to a region of the first nucleic acid and a first detectable label that has, in an uncomplexed state, a first detectable characteristic and, in a complexed state, a second detectable characteristic that differs from the first detectable characteristic;
      an amount of a reporter compound capable of forming complexes with the second nucleic acid, wherein each reporter compound comprises a binding portion specific to a region of the second nucleic acid and a second detectable label; and
      a binding member capable of capturing the reporter compound, wherein forming of complexes of the second nucleic acid with the reporter compound inhibits capturing of the reporter compound by the binding member;
   (b) subjecting the first and/or second nucleic acid to amplification;
   (c) forming complexes each comprising a first nucleic acid and a FRET compound;
   (d) forming complexes of a subset of the amount of reporter compound with a second nucleic acid;
   (e) capturing a remaining subset of the amount of reporter compound not in complex with a second nucleic acid on the binding member;
   (f) determining a value indicative for the presence and/or amount of first nucleic acid captured by FRET compounds; and
   (g) determining a value indicative for the presence and/or amount of reporter compound captured on the binding member.

2. The method of claim 1, further comprising determining a value indicative for the presence and/or amount of second nucleic acid based on the value indicative for the presence and/or amount of reporter compound captured on the binding member.

3. The method of claim 1, wherein the first detectable label or second detectable label is a fluorescent label.

4. The method of claim 3, wherein the fluorescent label emits in a wavelength range of from 300 nm to 850 nm.

5. The method of claim 1, wherein the value indicative for the presence and/or amount of first nucleic acid captured by FRET compounds is determined in a complexed state of the FRET compounds.

6. The method of claim 1, wherein the first nucleic acid is an analyte.

7. The method of claim 1, wherein the second nucleic acid is selected from the group consisting of a second analyte and a control nucleic acid.

8. The method of claim 1, wherein the steps of (i) forming complexes each comprising a first nucleic acid and a FRET compound, (ii) forming complexes of a subset of the amount of reporter compound with at least a subset of the amount of second nucleic acid, and (iii) capturing a remaining subset of the amount of reporter compound not in complex with a second nucleic acid on the binding member are performed concomitantly.

9. The method of claim 1, wherein amplification of the first and second nucleic acid is initiated prior to the step of forming complexes of a subset of the amount of reporter compound with at least a subset of the amount of second nucleic acid.

10. The method of claim 9, wherein the second nucleic acid is selected from the group consisting of a positive amplification control and a negative amplification control.

11. The method of claim 1, wherein the binding member comprises one or more different reporter specific capture compounds being capable of capturing a reporter compound on the binding member.

12. The method of claim 11, wherein the reporter specific capture compounds are oligonucleotides.

13. The method of claim 11, wherein the different reporter specific capture compounds are arranged on different locations with respect to the binding member.

14. The method of claim 11, wherein the reporter compounds are captured on the binding member by forming complexes with the reporter specific capture compounds.

15. The method of claim 11, wherein at least a part of an interaction site of the reporter compound being capable of forming a complex with a second nucleic acid is also capable of forming a complex with a reporter specific capture compound.

16. The method of claim 11, wherein the reporter specific capture compounds and the second nucleic acid compete for forming a complex with the reporter compound.

17. The method of claim 1, further comprising subjecting the first and/or second nucleic acids to reverse transcription prior to subjecting them to amplification.

18. The method of claim 9, wherein the amplification is an isothermal amplification method.

19. The method of claim 1, wherein said first detectable label comprises a chromophore and the first detectable characteristic is a state where emission of the chromophore is present.

20. The method of claim 1, wherein said first detectable label comprises a chromophore and the second detectable characteristic is a state where emission of the chromophore is quenched.

* * * * *